(12) United States Patent
Yukawa et al.

(10) Patent No.: US 9,328,361 B2
(45) Date of Patent: May 3, 2016

(54) CORYNEFORM BACTERIUM TRANSFORMANT AND PROCESS FOR PRODUCING PHENOL USING THE SAME

(75) Inventors: Hideaki Yukawa, Kizugawa (JP); Masayuki Inui, Kizugawa (JP)

(73) Assignee: GREEN PHENOL DEVELOPMENT CO., LTD., Kyoto (JP)

( * ) Notice: Subject to any disclaimer, the term of this patent is extended or adjusted under 35 U.S.C. 154(b) by 58 days.

(21) Appl. No.: 13/821,212

(22) PCT Filed: Sep. 7, 2011

(86) PCT No.: PCT/JP2011/070325
§ 371 (c)(1),
(2), (4) Date: Apr. 18, 2013

(87) PCT Pub. No.: WO2012/033112
PCT Pub. Date: Mar. 15, 2012

(65) Prior Publication Data
US 2013/0203139 A1 Aug. 8, 2013

(30) Foreign Application Priority Data
Sep. 8, 2010 (JP) ................. 2010-201445

(51) Int. Cl.
| | | |
|---|---|---|
| C12P 7/22 | (2006.01) | |
| C12N 9/88 | (2006.01) | |
| C12N 9/90 | (2006.01) | |
| C12N 9/10 | (2006.01) | |
| C12N 1/21 | (2006.01) | |

(52) U.S. Cl.
CPC ............. *C12P 7/22* (2013.01); *C12N 9/1085* (2013.01); *C12N 9/88* (2013.01); *C12N 9/90* (2013.01); *C12Y 401/99002* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,185,262 A * | 2/1993 | Kohama et al. ............ 435/320.1 |
| 5,260,198 A * | 11/1993 | Iwamori et al. .............. 435/232 |
| 6,303,383 B1 * | 10/2001 | Nakamura et al. ........... 435/477 |
| 7,368,268 B2 * | 5/2008 | Murakami et al. ........... 435/145 |
| 8,685,703 B2 | 4/2014 | Yukawa et al. | |
| 2003/0219881 A1 | 11/2003 | Brigitte et al. | |
| 2005/0277179 A1 * | 12/2005 | Takai ................... C12N 9/001 435/108 |

FOREIGN PATENT DOCUMENTS

| JP | 63-222682 | 9/1988 |
|---|---|---|
| JP | 3240492 B2 | 10/1991 |
| JP | H04-218380 A | 8/1992 |
| JP | 9-279 | 1/1997 |
| JP | 2006262824 A | 10/2006 |
| JP | 2006320238 A | 11/2006 |
| WO | WO-2009154122 A1 | 12/2009 |
| WO | WO-2012/067174 A1 | 5/2012 |

OTHER PUBLICATIONS

Tyrosine phenol-lyase 4.1.99.2, Enzyme Handbook, Schomburg, Ed., 1990.*
Lee et al., Treatment of phenol-contaminated soil by Corynebacterium glutamicum and toxicity removal evaluation, J. Hazardous Materials, Jun. 2010, 182, 937-40.*
Ikeda et al, Metabolic Engineering to Produce Tyrosine or Phenylalanine in a Tryptophan-Producing Corynebacterium glutamicum Strain, Appl. Environ. Microbiol., 1992, 58, 781-85.*
GenBank, Accession No. M13774.1, 1993, www.ncbi.nih.gov.*
English-language translation of JP H03-240492, 1991.*
Liu et al., Corynebacterium glutamicum Contains 3-Deoxy-D-Arabino-Heptulosonate 7-Phosphate Synthases That Display Novel Biochemical Features, Appl. Environ. Micobiol., 2008, 74, 5497-5503.*
Brinkrolf et al., Transcriptional regulation of catabolic pathways for aromatic compounds in Corynebacterium glutamicum, Genetics Mol. Res., 2006, 5, 773-89.*
Enzyme Handbook, Phenol 2-monooxygenase, Springer-Verlag Berlin Heidelberg, 1994.*
International Preliminary Report on Patentability in corresponding PCT/JP2011/070325 dated Apr. 9, 2013. (English Translation).
Yukawa, "Sekai no Biorefinery Doko to Rite no Kenkyu Kaihatsu," *Chemical Industrial Economy*, 57(6): 49-54 (2010).
Wierckx et al., "Engineering of Solvent-Tolerant Pseudomonas putida S12 for Bioproduction of Phenol from Glucose," *Appl. Environ. Microbiol.*, 71(12): 8221-8227 (2005).
Wierckx et al., "Transcriptome Analysis of a Phenol-Producing Pseudomonas putida S12 Construct: Genetic and Physiological Basis for Improved Production," *J. Bacteriol.*, 190(8): 2822-2830 (2008).
Sakai et al., "Effect of Lignocellulose-Derived Inhibitors on Growth of and Ethanol Production by Growth-Arrested Corynebacterium glutamicum R," *Appl. Environ. Microbiol.*, 73(7) 2349-2353 (2007).
Lutke-Eversloh et al., Perspectives of biotechnological production of L-tyrosine and its applications, *Appl. Microbiol. Biotechnol.*, 77:751-762 (2007).
Li et al., "Genetic and biochemical identification of the chorismate mutase from Corynebacterium glutamicum," *Microbiology*, 155: 3382-3391 (2009).
Hsu et al., "Mutational Analysis of Feedback Inhibition and Catalytic Sites of Prephenate Dehydratase from Corynebacterium Glutamicum," *Arch Microbiol.* 181: 237-244 (2004).

(Continued)

*Primary Examiner* — Tekchand Saidha
*Assistant Examiner* — Todd M Epstein
(74) *Attorney, Agent, or Firm* — Marshall, Gerstein & Borun LLP

(57) ABSTRACT

A phenol-producing transformant is provided which can efficiently produce phenol from a saccharide. A gene which encodes an enzyme having tyrosine phenol-lyase activity is transferred into *Corynebacterium glutamicum* as a host. A process for producing phenol is provided having a step of reacting the transformant in a reaction mixture containing a saccharide under reducing conditions, and a step of collecting phenol from the reaction mixture.

8 Claims, 3 Drawing Sheets

(56) References Cited

OTHER PUBLICATIONS

Inui et al., "A RITE Perspective on Global Biorefinery R&D Trends," *Cellulose Commun.*, 16(4): 151-156 (2009).
Yukawa, "Biorefinery: World Trends and RITE's R&D," *Chemical Engineering of Japan*, 75(1): 23-25 (2011).
International Search Report in corresponding PCT/JP2011/070325 mailed Oct. 4, 2011.
Written Opinion of ISA in corresponding PCT/JP2011/070325 mailed Sep. 26, 2011.
Extended European Search Report in corresponding PCT/2011/070325 mailed Feb. 2, 2014.
Ishige et al., "Whole Organism Biocatalysis," *Current Opinion in Chemical Biology*, vol. 9, pp. 174-180 (2005).
Kirchner et al., "Phenol Hydroxylase from Bacillus thermoglucosidasius A7, a Two-protein Component Monooxygenase with a Dual Role for FAD*", *Journal of Biological Chemistry*, vol. 278, No. 48, pp. 47545-47553 (2003).
Antson et al., Three-Dimensional Structure of Tyrosine Phenol-lyase, Biochemistry 1993, pp. 4195-4206.
GenBank Accession No. NC011830, Desulfitobacterium hafniense DCB-2, complete genome.
GenBank Accession No. CP000909, Chloroflexus aurantiacus J-10-fl, complete genome.
GenBank Accession No. CP001037, Nostoc punctiforme PCC 73102, complete genome.
GenBank Accession No. AE017226, Treponema denticola ATCC 35405, complete genome.
Youn Lee et al., Treatment of phenol-contaminated soil by Corynebacterium glutamicum and toxicity removal evaluation, Journal of Hazardous Materials 182 (2010), pp. 937-940.
Maruo et al., ügKoso Handboküh Asakura Shoten, pp. 180 (1983). (Partial English Translation).
Ikeda et al., Metabolic Engineering to Produce Tyrosine or Phenylalanine in a Tryptophan-Producing Corynebacterium glutamicum Strain, Appl. Environ. Microbiol., 1992, pp. 781-785.

\* cited by examiner

Influence of phenol on aerobic proliferation

Influence of phenol on saccharometabolism under reducing conditions

SEQUENCE LISTING

<160> NUMBER OF SEQ ID NOS: 67

<210> SEQ ID NO 1
<211> LENGTH: 1195
<212> TYPE: DNA
<213> ORGANISM: Artificial sequence
<220> FEATURE:
<223> OTHER INFORMATION: pCASE1-ori

<400> SEQUENCE: 1

```
atgaaaaccg accgtgcacg ctcgtgtgag aaagtcagct acatgagacc aactacccgc      60
cctgagggac gctttgagca gctgtggctg ccgctgtggc cattggcaag cgatgacctc     120
cgtgagggca tttaccgcac ctcacggaag aacgcgctgg ataagcgcta cgtcgaagcc     180
aatcccgacg cgctctctaa cctcctggtc gttgacatcg accaggagga cgcgcttttg     240
cgctctttgt gggacaggga ggactggaga cctaacgcgg tggttgaaaa ccccttaaac     300
gggcacgcac acgctgtctg ggcgctcgcg gagccattta cccgcaccga atacgccaaa     360
cgcaagcctt tggcctatgc cgcggctgtc accgaaggcc tacggcgctc tgtcgatggc     420
gatagcggat actccgggct gatcaccaaa aaccccgagc acactgcatg ggatagtcac     480
tggatcaccg ataagctgta tacgctcgat gagctgcgct tttggctcga agaaaccggc     540
tttatgccgc ctgcgtcctg gaggaaaacg cggcggttct cgccagttgg tctaggtcgt     600
aattgcgcac tcttttgaaag cgcacgtacg tgggcatatc gggaggtcag aaagcattt     660 ggagacgctg acggcctagg ccgcgcaatc caaaccaccg cgcaagcact taaccaagag     720
ctgtttgatg aaccactacc tgtggccgaa gttgactgta ttgccaggtc aatccataaa     780
tggatcatca ccaagtcacg catgtggaca gacggcgccg ccgtctacga cgccacattc     840
accgcaatgc aatccgcacg cgggaagaaa ggctggcaac gaagcgctga ggtgcgtcgt     900
gaggctggac atactctttg gaggaacatt ggctaaggtt tatgcacgtt atccacgcaa     960
cggaaaaaca gcccgcgagc tggcagaacg tgccggtatg tcggtgagaa cagctcaacg    1020
atggacttcc gaaccgcgtg aagtgttcat taaacgtgcc aacgagaagc gtgctcgcgt    1080
ccaggagctg cgcgccaaag gtctgtccat gcgcgctatc gcggcagaga ttggttgctc    1140
ggtgggcacg gttcaccgct acgtcaaaga agttgaagag aagaaaaccg cgtaa         1195
```

<210> SEQ ID NO 2
<211> LENGTH: 2675
<212> TYPE: DNA
<213> ORGANISM: Artificial sequence
<220> FEATURE:
<223> OTHER INFORMATION: pHSG298

<400> SEQUENCE: 2

```
gaggtctgcc tcgtgaagaa ggtgttgctg actcatacca ggcctgaatc gccccatcat      60
ccagccagaa agtgagggag ccacggttga tgagagcttt gttgtaggtg gaccagttgg     120
```

-continued

```
tgattttgaa cttttgcttt gccacggaac ggtctgcgtt gtcgggaaga tgcgtgatct      180
gatccttcaa ctcagcaaaa gttcgattta ttcaacaaag ccacgttgtg tctcaaaatc      240
tctgatgtta cattgcacaa gataaaaata tatcatcatg aacaataaaa ctgtctgctt      300
acataaacag taatacaagg ggtgttatga gccatattca acgggaaacg tcttgctcga      360
agccgcgatt aaattccaac atggatgctg atttatatgg gtataaatgg gctcgcgata      420
atgtcgggca atcaggtgcg acaatctatc gattgtatgg gaagcccgat gcgccagagt      480
tgtttctgaa acatggcaaa ggtagcgttg ccaatgatgt tacagatgag atggtcagac      540
taaactggct gacggaattt atgcctcttc cgaccatcaa gcattttatc cgtactcctg      600
atgatgcatg gttactcacc actgcgatcc ccgggaaaac agcattccag gtattagaag      660
aatatcctga ttcaggtgaa atattgttg atgcgctggc agtgttcctg cgccggttgc      720
attcgattcc tgtttgtaat tgtccttttt a acagcgatcg cgtatttcgt ctcgctcagg      780
cgcaatcacg aatgaataac ggtttggttg atgcgagtga ttttgatgac gagcgtaatg      840
gctggcctgt tgaacaagtc tggaaagaaa tgcataagct tttgccattc tcaccggatt      900
cagtcgtcac tcatggtgat ttctcacttg ataaccttat ttttgacgag gggaaattaa      960
taggttgtat tgatgttgga cgagtcggaa tcgcagaccg ataccaggat cttgccatcc     1020
tatggaactg cctcggtgag ttttctcctt cattacagaa acggctttt caaaaatatg     1080 gtattgataa tcctgatatg aataaattgc agtttcattt gatgctcgat gagttttct     1140 aatcagaatt ggttaattgg ttgtaacact ggcagagcat acgctgact tgacgggacg     1200 gcggctttgt tgaataaatc gcattcgcca ttcaggctgc gcaactgttg ggaagggcga     1260
tcggtgcggg cctcttcgct attacgccag ctggcgaaag ggggatgtgc tgcaaggcga     1320
ttaagttggg taacgccagg gttttcccag tcacgacgtt gtaaaacgac ggccagtgcc     1380
aagcttgcat gcctgcaggt cgactctaga ggatcccgg gtaccgagct cgaattcgta     1440
atcatgtcat agctgtttcc tgtgtgaaat tgttatccgc tcacaattcc acacaacata     1500
cgagccggaa gcataaagtg taaagcctgg ggtgcctaat gagtgagcta actcacatta     1560
attgcgttgc gctcactgcc cgcttttcag tcgggaaacc tgtcgtgcca gctgcattaa     1620
tgaatcggcc aacgcgcggg gagaggcggt ttgcgtattg gcgaactttt gctgagttga     1680
aggatcagat cacgcatctt cccgacaacg cagaccgttc cgtggcaaag caaaagttca     1740
aaatcagtaa ccgtcagtgc cgataagttc aaagttaaac ctggtgttga taccaacatt     1800
gaaacgctga tcgaaaacgc gctgaaaaac gctgctgaat gtgcgagctt cttccgcttc     1860
ctcgctcact gactcgctgc gctcggtcgt tcggctgcgg cgagcggtat cagctcactc     1920
aaaggcggta atacggttat ccacagaatc agggggataac gcaggaaaga acatgtgagc     1980
aaaaggccag caaaaggcca ggaaccgtaa aaaggccgcg ttgctggcgt ttttccatag     2040
gctccgcccc cctgacgagc atcacaaaaa tcgacgctca agtcagaggt ggcgaaaccc     2100
gacaggacta taaagatacc aggcgtttcc ccctggaagc tccctcgtgc gctctcctgt     2160
tccgaccctg ccgcttaccg gatacctgtc cgcctttctc ccttcgggaa gcgtggcgct     2220
ttctcaatgc tcacgctgta ggtatctcag ttcggtgtag gtcgttcgct ccaagctggg     2280
ctgtgtgcac gaaccccccg ttcagcccga ccgctgcgcc ttatccggta actatcgtct     2340
tgagtccaac ccggtaagac acgacttatc gccactggca gcagccactg gtaacaggat     2400
tagcagagcg aggtatgtag gcggtgctac agagttcttg aagtggtggc ctaactacgg     2460
ctacactaga aggacagtat ttggtatctg cgctctgctg aagccagtta ccttcggaaa     2520
```

```
aagagttggt agctcttgat ccggcaaaca aaccaccgct ggtagcggtg gtttttttgt    2580
ttgcaagcag cagattacgc gcagaaaaaa aggatctcaa gaagatcctt tgatcttttc    2640
tacggggtct gacgctcagt ggaacgatcc gtcga                               2675

<210> SEQ ID NO 3
<211> LENGTH: 25
<212> TYPE: DNA
<213> ORGANISM: Artificial sequence
<220> FEATURE:
<223> OTHER INFORMATION: PCR primer

<400> SEQUENCE: 3
atagatctag aacgtccgta ggagc                                            25

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
atagatctga cttggttacg atggac                                           26

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
atagatctag gtttcccgac tggaaag                                          27

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
atagatctcg tgccagctgc attaatga                                         28

<210> SEQ ID NO 7
<211> LENGTH: 1885
<212> TYPE: DNA
<213> ORGANISM: Artificial sequence
<220> FEATURE:
<223> OTHER INFORMATION: pCG1-ori

<400> SEQUENCE: 7
agcatggtcg tcacagagct ggaagcggca gcgagaatta ccgcgatcg tggcgcggtg       60 cccgcaggca tgacaaacat cgtaaatgcc gcgtttcgtg tggccgtggc cgcccaggac     120
gtgtcagcgc cgccaccacc tgcaccgaat cggcagcagc gtcgcgcgtc gaaaaagcgc     180
acaggcggca agaagcgata gctgcacga atacctgaaa aatgttgaac gccccgtgag     240
cggtaactca cagggcgtcg gctaacccca gtccaaacc tgggagaaag cgctcaaaaa     300
tgactctagc ggattcacga gacattgaca caccggcctg gaaatttttcc gctgatctgt    360 tcgacaccca tcccgagctc gcgctgcgat cacgtggctg gacgagcgaa gaccgccgcg    420
```

| | |
|---|---|
| aattcctcgc tcacctgggc agagaaaatt tccagggcag caagacccgc gacttcgcca | 480 |
| gcgcttggat caaagacccg gacacgggag aaacacagcc gaagttatac cgagttggtt | 540 |
| caaaatcgct tgcccggtgc cagtatgttg ctctgacgca cgcgcagcac gcagccgtgc | 600 |
| ttgtcctgga cattgatgtg ccgagccacc aggccggcgg gaaaatcgag cacgtaaacc | 660 |
| ccgaggtcta cgcgattttg gagcgctggg cacgcctgga aaaagcgcca gcttggatcg | 720 |
| gcgtgaatcc actgagcggg aaatgccagc tcatctggct cattgatccg gtgtatgccg | 780 |
| cagcaggcat gagcagcccg aatatgcgcc tgctggctgc aacgaccgag gaaatgaccc | 840 |
| gcgtttttcgg cgctgaccag gcttttttcac ataggctgag ccggtggcca ctgcacgtct | 900 |
| ccgacgatcc caccgcgtac cgctggcatg cccagcacaa tcgcgtggat cgcctagctg | 960 |
| atcttatgga ggttgctcgc atgatctcag gcacagaaaa acctaaaaaa cgctatgagc | 1020 |
| aggagttttc tagcggacgg gcacgtatcg aagcggcaag aaaagccact gcggaagcaa | 1080 |
| aagcacttgc cacgcttgaa gcaagcctgc cgagcgccgc tgaagcgtct ggagagctga | 1140 |
| tcgacggcgt ccgtgtcctc tggactgctc cagggcgtgc cgcccgtgat gagacggctt | 1200 |
| ttcgccacgc tttgactgtg ggataccagt taaaagcggc tggtgagcgc ctaaaagaca | 1260 |
| ccaagatcat cgacgcctac gagcgtgcct acaccgtcgc tcaggcggtc ggagcagacg | 1320 |
| gccgtgagcc tgatctgccg ccgatgcgtg accgccagac gatggcgcga cgtgtgcgcg | 1380 |
| gctacgtcgc taaaggccag ccagtcgtcc ctgctcgtca gacagagacg cagagcagcc | 1440 |
| gagggcgaaa agctctggcc actatgggaa gacgtggcgg taaaaaggcc gcagaacgct | 1500 |
| ggaaagaccc aaacagtgag tacgcccgag cacagcgaga aaaactagct aagtccagtc | 1560 |
| aacgacaagc taggaaagct aaaggaaatc gcttgaccat tgcaggttgg tttatgactg | 1620 |
| ttgagggaga gactggctcg tggccgacaa tcaatgaagc tatgtctgaa tttagcgtgt | 1680 |
| cacgtcagac cgtgaataga gcacttaagt ctgcgggcat tgaacttcca cgaggacgcc | 1740 |
| gtaaagcttc ccagtaaatg tgccatctcg taggcagaaa acggttcccc ccgtaggggt | 1800 |
| ctctctcttg gcctcctttc taggtcgggc tgattgctct tgaagctctc tagggggggct | 1860 |
| cacaccatag gcagataacg gttcc | 1885 |

<210> SEQ ID NO 8
<211> LENGTH: 2227
<212> TYPE: DNA
<213> ORGANISM: Artificial sequence
<220> FEATURE:
<223> OTHER INFORMATION: pHSG398

<400> SEQUENCE: 8

| | |
|---|---|
| acggaagatc acttcgcaga ataaataaat cctggtgtcc ctgttgatac cgggaagccc | 60 |
| tgggccaact tttggcgaaa atgagacgtt gatcggcacg taagaggttc caactttcac | 120 |
| cataatgaaa taagatcact accgggcgta ttttttgagt tatcgagatt ttcaggagct | 180 |
| aaggaagcta aaatggagaa aaaaatcact ggatatacca ccgttgatat atcccaatgg | 240 |
| catcgtaaag aacattttga ggcatttcag tcagttgctc aatgtaccta taaccagacc | 300 |
| gttcagctgg atattacggc cttttttaaag accgtaaaga aaataagcaa caagttttat | 360 |
| ccggccttta ttcacattct tgcccgcctg atgaatgctc atccggaatt tcgtatggca | 420 |
| atgaaagacg gtgagctggt gatatgggat agtgttcacc cttgttacac cgttttccat | 480 |
| gagcaaactg aaacgttttc atcgctctgg agtgaatacc acgacgattt ccggcagttt | 540 |
| ctacacatat attcgcaaga tgtggcgtgt tacggtgaaa acctggccta tttccctaaa | 600 |

```
gggtttattg agaatatgtt tttcgtctca gccaatccct gggtgagttt caccagtttt    660
gatttaaacg tggccaatat ggacaacttc ttcgccccg ttttcaccat gggcaaatat    720
tatacgcaag gcgacaaggt gctgatgccg ctggcgattc aggttcatca tgccgtctgt    780
gatggcttcc atgtcggcag aatgcttaat gaattacaac agtactgcga tgagtggcag    840
ggcggggcgt aatttttta aggcagttat tggtgccctt aaacgcctgg tgctacgcct    900
gaataagtga taataagcgg atgaatggca gaaattcagc ttgggcccagt gccaagctcc    960
aatacgcaaa ccgcctctcc ccgcgcgttg gccgattcat taatgcagct ggcacgacag   1020
gtttcccgac tggaaagcgg gcagtgagcg caacgcaatt aatgtgagtt agctcactca   1080
ttaggcaccc caggctttac actttatgct tccggctcgt atgttgtgtg gaattgtgag   1140
cggataacaa tttcacacag gaaacagcta tgaccatgat tacgaattcg agctcggtac   1200
ccggggatcc tctagagtcg acctgcaggc atgcaagctt ggcactggcc gtcgttttac   1260
aacgtcgtga ctgggaaaac cctggcgtta cccaacttaa tcgccttgca gcacatcccc   1320
ctttcgccag ctggcgtaat agcgaagagg cccgcaccga tcgcccttcc caacagttgc   1380
gcagcctgaa tggcgaatga gcttcttccg cttcctcgct cactgactcg ctgcgctcgg   1440
tcgttcggct gcggcgagcg gtatcagctc actcaaaggc ggtaatacgg ttatccacag   1500
aatcagggga taacgcagga agaacatgt gagcaaaagg ccagcaaaag gccaggaacc   1560
gtaaaaaggc cgcgttgctg gcgttttttcc ataggctccg ccccctgac gagcatcaca   1620
aaaatcgacg ctcaagtcag aggtggcgaa acccgacagg actataaaga taccaggcgt   1680
ttccccctgg aagctccctc gtgcgctctc ctgttccgac cctgccgctt accggatacc   1740
tgtccgcctt tctcccttcg ggaagcgtgg cgctttctca atgctcacgc tgtaggtatc   1800
tcagttcggt gtaggtcgtt cgctccaagc tgggctgtgt gcacgaaccc ccgttcagc    1860
ccgaccgctg cgccttatcc ggtaactatc gtcttgagtc aacccggta agacacgact   1920
tatcgccact ggcagcagcc actggtaaca ggattagcag agcgaggtat gtaggcggtg   1980
ctacagagtt cttgaagtgg tggcctaact acggctacac tagaaggaca gtatttggta   2040
tctgcgctct gctgaagcca gttaccttcg gaaaaagagt tggtagctct tgatccggca   2100
acaaaccac cgctggtagc ggtggttttt tgtttgcaa gcagcagatt acgcgcagaa   2160
aaaaggatc tcaagaagat cctttgatct tttctacggg gtctgacgct cagtggaact   2220
ccgtcga                                                            2227
```

<210> SEQ ID NO 9
<211> LENGTH: 26
<212> TYPE: DNA
<213> ORGANISM: Artificial sequence
<220> FEATURE:
<223> OTHER INFORMATION: PCR primer

<400> SEQUENCE: 9
atagatctag catggtcgtc acagag                                         26

<210> SEQ ID NO 10
<211> LENGTH: 28
<212> TYPE: DNA
<213> ORGANISM: Artificial sequence
<220> FEATURE:
<223> OTHER INFORMATION: PCR primer

<400> SEQUENCE: 10

| | |
|---|---|
| atagatctgg aaccgttatc tgcctatg | 28 |

<210> SEQ ID NO 11
<211> LENGTH: 28
<212> TYPE: DNA
<213> ORGANISM: Artificial sequence
<220> FEATURE:
<223> OTHER INFORMATION: PCR primer

<400> SEQUENCE: 11

| | |
|---|---|
| atagatctgt cgaacggaag atcacttc | 28 |

<210> SEQ ID NO 12
<211> LENGTH: 26
<212> TYPE: DNA
<213> ORGANISM: Artificial sequence
<220> FEATURE:
<223> OTHER INFORMATION: PCR primer

<400> SEQUENCE: 12

| | |
|---|---|
| atagatctag ttccactgag cgtcag | 26 |

<210> SEQ ID NO 13
<211> LENGTH: 4125
<212> TYPE: DNA
<213> ORGANISM: Artificial sequence
<220> FEATURE:
<223> OTHER INFORMATION: pCRB11

<400> SEQUENCE: 13

| | |
|---|---|
| ctgtcgaacg gaagatcact tcgcagaata aataaatcct ggtgtccctg ttgataccgg | 60 |
| gaagccctgg gccaacttTt ggcgaaaatg agacgttgat cggcacgtaa gaggttccaa | 120 |
| ctttcaccat aatgaaataa gatcactacc gggcgtattt tttgagttat cgagattttc | 180 |
| aggagctaag gaagctaaaa tggagaaaaa aatcactgga tataccaccg ttgatatatc | 240 |
| ccaatggcat cgtaaagaac attttgaggc atttcagtca gttgctcaat gtacctataa | 300 |
| ccagaccgtt cagctggata ttacggcctt tttaaagacc gtaaagaaaa ataagcacaa | 360 |
| gttttatccg gcctttattc acattcttgc ccgcctgatg aatgctcatc cggaatttcg | 420 |
| tatggcaatg aaagacggtg agctggtgat atgggatagt gttcacccTt gttacaccgt | 480 |
| tttccatgag caaactgaaa cgttttcatc gctctggagt gaataccacg acgatttccg | 540 |
| gcagtttcta cacatatatt cgcaagatgt ggcgtgttac ggtgaaaacc tggcctattt | 600 |
| ccctaaaggg tttattgaga atatgttttt cgtctcagcc aatccctggg tgagtttcac | 660 |
| cagttttgat ttaaacgtgg ccaatatgga caacttcttc gcccccgttt tcaccatggg | 720 |
| caaatattat acgcaaggcg acaaggtgct gatgccgctg gcgattcagg ttcatcatgc | 780 |
| cgtttgtgat ggcttccatg tcggcagaat gcttaatgaa ttacaacagt actgcgatga | 840 |
| gtggcagggc ggggcgtaat ttttttaagg cagttattgg tgcccttaaa cgcctggttg | 900 |
| ctacgcctga ataagtgata taagcggat gaatggcaga aattcagctt ggcccagtgc | 960 |
| caagctccaa tacgcaaacc gcctctcccc gcgcgttggc cgattcatta atgcagctgg | 1020 |
| cacgacaggt ttcccgactg gaaagcgggc agtgagcgca acgcaattaa tgtgagttag | 1080 |
| ctcactcatt aggcacccca ggctttacac tttatgcttc cggctcgtat gttgtgtgga | 1140 |
| attgtgagcg gataacaatt tcacacagga aacagctatg accatgatta cgaattcgag | 1200 |
| ctcggtaccc ggggatcctc tagagtcgac ctgcaggcat gcaagcttgg cactggccgt | 1260 |
| cgttttacaa cgtcgtgact gggaaaaccc tggcgttacc caacttaatc gccttgcagc | 1320 |

-continued

```
acatccccct tcgccagct ggcgtaatag cgaagaggcc cgcaccgatc gcccttccca    1380
acagttgcgc agcctgaatg gcgaatgagc ttcttccgct tcctcgctca ctgactcgct    1440
gcgctcggtc gttcggctgc ggcgagcggt atcagctcac tcaaaggcgg taatacggtt    1500
atccacagaa tcaggggata acgcaggaaa gaacatgtga gcaaaaggcc agcaaaaggc    1560
caggaaccgt aaaaaggccg cgttgctggc gtttttccat aggctccgcc cccctgacga    1620
gcatcacaaa aatcgacgct caagtcagag gtggcgaaac ccgacaggac tataaagata    1680
ccaggcgttt ccccctggaa gctccctcgt gcgctctcct gttccgaccc tgccgcttac    1740
cggatacctg tccgcctttc tcccttcggg aagcgtggcg ctttctcata gctcacgctg    1800
taggtatctc agttcggtgt aggtcgttcg ctccaagctg ggctgtgtgc acgaaccccc    1860
cgttcagccc gaccgctgcg ccttatccgg taactatcgt cttgagtcca acccggtaag    1920
acacgactta tcgccactgg cagcagccac tggtaacagg attagcagag cgaggtatgt    1980
aggcggtgct acagagttct tgaagtggtg gcctaactac ggctacacta agaacagt    2040 atttggtatc tgcgctctgc tgaagccagt taccttcgga aaaagagttg gtagctcttg    2100
atccggcaaa caaccaccg ctggtagcgg tggtttttttt gtttgcaagc agcagattac    2160
gcgcagaaaa aaggatctca agaagatcc tttgatcttt tctacggggt ctgacgctca    2220
gtggaactag atctagcatg gtcgtcacag agctggaagc ggcagcgaga attatccgcg    2280
atcgtggcgc ggtgcccgca ggcatgacaa acatcgtaaa tgccgcgttt cgtgtggccg    2340
tggccgccca ggacgtgtca gcgccgccac cacctgcacc gaatcggcag cagcgtcgcg    2400
cgtcgaaaaa gcgcacaggc ggcaagaagc gataagctgc acgaatacct gaaaaatgtt    2460
gaacgccccg tgagcggtaa ctcacagggc gtcggctaac ccccagtcca aacctgggag    2520
aaagcgctca aaaatgactc tagcggattc acgagacatt gacacaccgg cctggaaatt    2580
ttccgctgat ctgttcgaca cccatcccga gctcgcgctg cgatcacgtg gctggacgag    2640
cgaagaccgc cgcgaattcc tcgctcacct gggcagagaa aatttccagg gcagcaagac    2700
ccgcgacttc gccagcgctt ggatcaaaga cccggacacg ggagaaacac agccgaagtt    2760
ataccgagtt ggttcaaaat cgcttgcccg gtgccagtat gttgctctga cgcacgcgca    2820
gcacgcagcc gtgcttgtcc tggacattga tgtgccgagc caccaggccg gcgggaaaat    2880
cgagcacgta aaccccgagg tctacgcgat tttggagcgc tgggcacgcc tggaaaaagc    2940
gccagcttgg atcggcgtga atccactgag cgggaaatgc agctcatct ggctcattga    3000 tccggtgtat gccgcagcag gcatgagcag cccgaatatg cgcctgctgg ctgcaacgac    3060
cgaggaaatg acccgcgttt tcggcgctga ccaggctttt tcacataggc tgagccggtg    3120
gccactgcac gtctccgacg atcccaccgc gtaccgctgg catgcccagc acaatcgcgt    3180
ggatcgccta gctgatctta tggaggttgc tcgcatgatc tcaggcacag aaaaacctaa    3240
aaaacgctat gagcaggagt tttctagcgg acgggcacgt atcgaagcgg caagaaaagc    3300
cactgcggaa gcaaaagcac ttgccacgct tgaagcaagc ctgccgagcg ccgctgaagc    3360
gtctggagag ctgatcgacg gcgtccgtgt cctctggact gctccagggc gtgccgcccg    3420
tgatgagacg gcttttcgcc acgctttgac tgtgggatac cagttaaaag cggctggtga    3480
gcgcctaaaa gacaccaaga tcatcgacgc ctacgagcgt gcctacaccg tcgctcaggc    3540
ggtcggagca gacggccgtg agcctgatct gccgccgatg cgtgaccgcc agacgatggc    3600
gcgacgtgtg cgcggctacg tcgctaaagg ccagccagtc gtccctgctc gtcagacaga    3660
```

```
gacgcagagc agccgagggc gaaaagctct ggccactatg ggaagacgtg gcggtaaaaa    3720
ggccgcagaa cgctggaaag acccaaacag tgagtacgcc cgagcacagc gagaaaaact    3780
agctaagtcc agtcaacgac aagctaggaa agctaaagga aatcgcttga ccattgcagg    3840
ttggtttatg actgttgagg gagagactgg ctcgtggccg acaatcaatg aagctatgtc    3900
tgaatttagc gtgtcacgtc agaccgtgaa tagagcactt aagtctgcgg gcattgaact    3960
tccacgagga cgccgtaaag cttcccagta aatgtgccat ctcgtaggca gaaaacggtt    4020
ccccccgtag gggtctctct cttggcctcc tttctaggtc gggctgattg ctcttgaagc    4080
tctctagggg ggctcacacc ataggcagat aacggttcca gatct                    4125
```

<210> SEQ ID NO 14
<211> LENGTH: 465
<212> TYPE: DNA
<213> ORGANISM: Artificial sequence
<220> FEATURE:
<223> OTHER INFORMATION: Zeocin resistant gene

<400> SEQUENCE: 14

```
tagcttatcc tcagtcctgc tcctctgcca caaagtgcac gcagttgccg gccgggtcgc      60
gcagggcgaa ctcccgcccc cacggctgct cgccgatctc ggtcatggcc ggcccggagg     120
cgtcccggaa gttcgtggac acgacctccg accactcggc gtacagctcg tccaggccgc     180
gcacccacac ccaggccagg gtgttgtccg gcaccacctg gtcctggacc gcgctgatga     240
acagggtcac gtcgtcccgg accacaccgg cgaagtcgtc ctccacgaag tcccgggaga     300
acccgagccg gtcggtccag aactcgaccg ctccggcgac gtcgcgcgcg gtgagcaccg     360
gaacggcact ggtcaacttg gccatgatgg ccctcctata gtgagtcgta ttatactatg     420
ccgatatact atgccgatga ttaattgtca aaacagcgtg gatgg                     465
```

<210> SEQ ID NO 15
<211> LENGTH: 28
<212> TYPE: DNA
<213> ORGANISM: Artificial sequence
<220> FEATURE:
<223> OTHER INFORMATION: PCR primer

<400> SEQUENCE: 15

```
atgatatccg aagtgatctt ccgttcga                                         28
```

<210> SEQ ID NO 16
<211> LENGTH: 28
<212> TYPE: DNA
<213> ORGANISM: Artificial sequence
<220> FEATURE:
<223> OTHER INFORMATION: PCR primer

<400> SEQUENCE: 16

```
atgatatcaa ggcagttatt ggtgccct                                         28
```

<210> SEQ ID NO 17
<211> LENGTH: 28
<212> TYPE: DNA
<213> ORGANISM: Artificial sequence
<220> FEATURE:
<223> OTHER INFORMATION: PCR primer

<400> SEQUENCE: 17

```
atgatatcta gcttatcctc agtcctgc                                         28
```

```
<210> SEQ ID NO 18
<211> LENGTH: 28
<212> TYPE: DNA
<213> ORGANISM: Artificial sequence
<220> FEATURE:
<223> OTHER INFORMATION: PCR primer

<400> SEQUENCE: 18
atgatatccc atccacgctg ttttgaca                                              28

<210> SEQ ID NO 19
<211> LENGTH: 551
<212> TYPE: DNA
<213> ORGANISM: Artificial sequence
<220> FEATURE:
<223> OTHER INFORMATION: PgapA

<400> SEQUENCE: 19
ccgaagatct gaagattcct gatacaaatt ctgttgtgac ggaagatttg ttggaagaaa            60
tctagtcgct cgtctcataa aaacgaccga gcctattggg attaccattg aagccagtgt          120
gagttgcatc acactggctt caaatctgag actttacttt gtggattcac ggggggtgtag          180 tgcaattcat aattagcccc attcggggga gcagatcgcg gcgcgaacga tttcaggttc          240
gttccctgca aaactatttt agcgcaagtg ttggaaatgc cccgtctgg ggtcaatgtc           300 tattttttgaa tgtgtttgta tgattttgaa tccgctgcaa aatctttgtt tccccgctaa         360
agttggggac aggttgacac ggagttgact cgacgaatta tccaatgtga gtaggtttgg          420
tgcgtgagtt ggaaaatttc gccatactcg cccttgggtt ctgtcagctc aagaattctt          480
gagtgaccga tgctctgatt gacctaactg cttgacacat tgcattcct acaatcttta          540 gaggagacac a                                                              551

<210> SEQ ID NO 20
<211> LENGTH: 425
<212> TYPE: DNA
<213> ORGANISM: Artificial sequence
<220> FEATURE:
<223> OTHER INFORMATION: terminator sequence

<400> SEQUENCE: 20
ctgttttggc ggatgagaga agattttcag cctgatacag attaaatcag aacgcagaag           60
cggtctgata aaacagaatt tgcctggcgg cagtagcgcg gtggtccac ctgaccccat           120 gccgaactca gaagtgaaac gccgtagcgc cgatggtagt gtggggtctc cccatgcgag          180
agtagggaac tgccaggcat caaataaaac gaaaggctca gtcgaaagac tgggcctttc          240
gttttatctg ttgtttgtcg gtgaacgctc tcctgagtag acaaatccg ccgggagcgg          300 atttgaacgt tgcgaagcaa cggcccggag ggtggcgggc aggacgcccg ccataaactg          360
ccaggcatca aattaagcag aaggccatcc tgacggatgg ccttttttgcg tttctacaaa         420 ctctt                                                                      425

<210> SEQ ID NO 21
<211> LENGTH: 31
<212> TYPE: DNA
<213> ORGANISM: Artificial sequence
<220> FEATURE:
<223> OTHER INFORMATION: PCR primer

<400> SEQUENCE: 21
ctctgtcgac ccgaagatct gaagattcct g                                         31
```

<210> SEQ ID NO 22
<211> LENGTH: 46
<212> TYPE: DNA
<213> ORGANISM: Artificial sequence
<220> FEATURE:
<223> OTHER INFORMATION: PCR primer

<400> SEQUENCE: 22
ctctgtcgac ggatccccat ggtgtgtctc tctaaagat tgtagg         46

<210> SEQ ID NO 23
<211> LENGTH: 36
<212> TYPE: DNA
<213> ORGANISM: Artificial sequence
<220> FEATURE:
<223> OTHER INFORMATION: PCR primer

<400> SEQUENCE: 23
ctctgcatgc ccatggctgt tttggcggat gagaga         36

<210> SEQ ID NO 24
<211> LENGTH: 41
<212> TYPE: DNA
<213> ORGANISM: Artificial sequence
<220> FEATURE:
<223> OTHER INFORMATION: PCR primer

<400> SEQUENCE: 24
ctctgcatgc tcatgaaaga gtttgtagaa acgcaaaaag g         41

<210> SEQ ID NO 25
<211> LENGTH: 5118
<212> TYPE: DNA
<213> ORGANISM: Artificial sequence
<220> FEATURE:
<223> OTHER INFORMATION: pCRB207

<400> SEQUENCE: 25

| | |
|---|---|
| agatctaggt ttcccgactg gaaagcgggc agtgagcgca acgcaattaa tgtgagttag | 60 |
| ctcactcatt aggcacccca ggctttacac tttatgcttc cggctcgtat gttgtgtgga | 120 |
| attgtgagcg ataacaatt tcacacagga aacagctatg accatgatta cgaattcgag | 180 |
| ctcggtaccc ggggatcctc tagagtcgac ccgaagatct gaagattcct gatcaaatt | 240 |
| ctgttgtgac ggaagatttg ttggaagaaa tctagtcgct cgtctcataa aaacgaccga | 300 |
| gcctattggg attaccattg aagccagtgt gagttgcatc acactggctt caaatctgag | 360 |
| actttacttt gtggattcac gggggtgtag tgcaattcat aattagcccc attcggggga | 420 |
| gcagatcgcg gcgcgaacga tttcaggttc gttccctgca aaaactattt agcgcaagtg | 480 |
| ttggaaatgc ccccgtctgg ggtcaatgtc tatttttgaa tgtgtttgta tgattttgaa | 540 |
| tccgctgcaa aatctttgtt tccccgctaa agttggggac aggttgacac ggagttgact | 600 |
| cgacgaatta tccaatgtga gtaggtttgg tgcgtgagtt ggaaaatttc gccatactcg | 660 |
| cccttgggtt ctgtcagctc aagaattctt gagtgaccga tgctctgatt gacctaactg | 720 |
| cttgacacat tgcatttcct acaatcttta gaggagacac accatggctg ttttggcgga | 780 |
| tgagagaaga ttttcagcct gatacagatt aaatcagaac gcagaagcgg tctgataaaa | 840 |
| cagaatttgc ctggcggcag tagcgcggtg gtcccacctg accccatgcc gaactcagaa | 900 |
| gtgaaacgcc gtagcgccga tggtagtgtg ggtctcccc atgcgagagt agggaactgc | 960 |
| caggcatcaa ataaaacgaa aggctcagtc gaaagactgg gcctttcgtt ttatctgttg | 1020 |

```
tttgtcggtg aacgctctcc tgagtaggac aaatccgccg ggagcggatt tgaacgttgc   1080
gaagcaacgg cccggagggt ggcgggcagg acgcccgcca taaactgcca ggcatcaaat   1140
taagcagaag gccatcctga cggatggcct ttttgcgttt ctacaaactc tttcatgggg   1200
atccgtcgac ctgcaggcat gcaagcttgg cactggccgt cgttttacaa cgtcgtgact   1260
gggaaaaccc tggcgttacc caacttaatc gccttgcagc acatccccct ttcgccagct   1320
ggcgtaatag cgaagaggcc cgcaccgatc gcccttccca cagttgcgc agcctgaatg    1380
gcgaatgcga tttattcaac aaagccgccg tcccgtcaag tcagcgtaat gctctgccag   1440
tgttacaacc aattaaccaa ttctgattag aaaaactcat cgagcatcaa atgaaactgc   1500
aatttattca tatcaggatt atcaatacca tatttttgaa aaagccgttt ctgtaatgaa   1560
ggagaaaact caccgaggca gttccatagg atggcaagat cctggtatcg gtctgcgatt   1620
ccgactcgtc caacatcaat acaacctatt aatttcccct cgtcaaaaat aaggttatca   1680
agtgagaaat caccatgagt gacgactgaa tccggtgaga atggcaaaag cttatgcatt   1740
tctttccaga cttgttcaac aggccagcca ttacgctcgt catcaaaatc actcgcatca   1800
accaaaccgt tattcattcg tgattgcgcc tgagcgagac gaaatacgcg atcgctgtta   1860
aaaggacaat tacaaacagg aatcgaatgc aaccggcgca ggaacactgc cagcgcatca   1920
acaatatttt cacctgaatc aggatattct tctaatacct ggaatgctgt tttcccgggg   1980
atcgcagtgg tgagtaacca tgcatcatca ggagtacgga taaaatgctt gatggtcgga   2040
agaggcataa attccgtcag ccagtttagt ctgaccatct catctgtaac atcattggca   2100
acgctacctt tgccatgttt cagaaacaac tctggcgcat cgggcttccc atacaatcga   2160
tagattgtcg cacctgattg cccgacatta tcgcgagccc atttatacc atataaatca    2220
gcatccatgt tggaatttaa tcgcggcttc gagcaagacg tttcccgttg aatatggctc   2280
ataacacccc ttgtattact gtttatgtaa gcagacagtt ttattgttca tgatgatata   2340
tttttatctt gtgcaatgta acatcagaga ttttgagaca caacgtggct ttgttgaata   2400
aatcgaactt ttgctgagtt gaaggatcag atcacgcatc ttcccgacaa cgcagaccgt   2460
tccgtggcaa agcaaaagtt caaaatcacc aactggtcca cctacaacaa agctctcatc   2520
aaccgtggct ccctcacttt ctggctggat gatgggcga ttcaggcctg gtatgagtca    2580
gcaacacctt cttcacgagg cagacctctc gacggagttc cactgagcgt cagacccgt    2640
agaaagatc aaaggatctt cttgagatcc ttttttttctg cgcgtaatct gctgcttgca   2700
aacaaaaaaa ccaccgctac cagcggtggt ttgtttgccg gatcaagagc taccaactct   2760
ttttccgaag gtaactggct tcagcagagc gcagatacca atactgttc ttctagtgta    2820
gccgtagtta ggccaccact tcaagaactc tgtagcaccg cctacatacc tcgctctgct   2880
aatcctgtta ccagtggctg ctgccagtgg cgataagtcg tgtcttaccg ggttggactc   2940
aagacgatag ttaccggata aggcgcagcg gtcgggctga acggggggtt cgtgcacaca   3000
gcccagcttg gagcgaacga cctacaccga actgagatac ctacagcgtg agctatgaga   3060
aagcgccacg cttcccgaag ggagaaaggc ggacaggtat ccggtaagcg cagggtcgg    3120
aacaggagag cgcacgaggg agcttccagg gggaaacgcc tggtatcttt atagtcctgt   3180
cgggtttcgc cacctctgac ttgagcgtcg attttttgtga tgctcgtcag ggggcggag   3240
cctatggaaa aacgccagca acgcggcctt tttacggttc ctggccttttt gctggccttt  3300
tgctcacatg ttctttcctg cgttatcccc tgattctgtg gataaccgta ttaccgcctt   3360
```

```
tgagtgagct gataccgctc gccgcagccg aacgaccgag cgcagcgagt cagtgagcga    3420
ggaagcggaa gaagctcgca cattcagcag cgttttttcag cgcgttttcg atcaacgttt    3480
caatgttggt atcaacacca ggtttaactt tgaacttatc ggcactgacg gttactgatt    3540
ttgaactttt gctttgccac ggaacggtct gcgttgtcgg gaagatgcgt gatctgatcc    3600
ttcaactcag caaaagttcg ccaatacgca aaccgcctct ccccgcgcgt tggccgattc    3660
attaatgcag ctggcacgag atctgacttg gttacgatgg actttgaaca cgccgagggt    3720
gactaaaccg ctggatttac gcggttttct tctcttcaac ttctttgacg tagcggtgaa    3780
ccgtgcccac cgagcaacca atctctgccg cgatagcgcg catggacaga cctttggcgc    3840
gcagctcctg gacgcgagca cgcttctcgt tggcacgttt aatgaacact tcacgcggtt    3900
cggaagtcca tcgttgagct gttctcaccg acataccggc acgttctgcc agctcgcggg    3960 ctgttttttcc gttgcgtgga taacgtgcat aaaccttagc caatgttcct ccaaagagta    4020
tgtccagcct cacgacgcac ctcagcgctt cgttgccagc cttttcttccc gcgtgcggat    4080 tgcattgcgg tgaatgtggc gtcgtagacg gcggcgccgt ctgtccacat gcgtgacttg    4140
gtgatgatcc atttatggat tgacctggca atacagtcaa cttcggccac aggtagtggt    4200
tcatcaaaca gctcttggtt aagtgcttgc gcggtggttt ggattgcgcg gcctaggccg    4260
tcagcgtctc caaaatgctt tctgacctcc cgatatgccc acgtacgtgc gctttcaaag    4320
agtgcgcaat tacgacctag accaactggc gagaaccgcc gcgttttcct ccaggacgca    4380
ggcggcataa agccggtttc ttcgagccaa aagcgcagct catcgagcgt atacagctta    4440
tcggtgatcc agtgactatc ccatgcagtg tgctcggggt ttttggtgat cagcccggag    4500
tatccgctat cgccatcgac agagcgccgt aggccttcgg tgacagccgc ggcataggcc    4560
aaaggcttgc gtttggcgta ttcggtgcgg gtaaatggct ccgcgagcgc ccagacagcg    4620
tgtgcgtgcc cgtttaaggg gttttcaacc accgcgttag gtctccagtc ctccctgtcc    4680
cacaaagagc gcaaaagcgc gtcctcctgg tcgatgtcaa cgaccaggag gttagagagc    4740
gcgtcgggat tggcttcgac gtagcgctta tccagcgcgt tcttccgtga ggtgcggtaa    4800
atgccctcac ggaggtcatc gcttgccaat ggccacagcg gcagccacag ctgctcaaag    4860
cgtccctcag ggcgggtagt tggtctcatg tagctgactt tctcacacga gcgtgcacgg    4920
tcggttttca ttcataatac gacatttaac caagtcagat gttttcccgg tttccgggg    4980 ttccctgaa gaaccctttcc agtgcgagcg aagcgagctc ctttggccgg cgccctcag    5040 gtagccctct aaggctccca gggctccgcc cctccctgag gttggctcaa gcctcctggt    5100
ggctcctacg gacgttct                                                  5118
```

<210> SEQ ID NO 26
<211> LENGTH: 29
<212> TYPE: DNA
<213> ORGANISM: Artificial sequence
<220> FEATURE:
<223> OTHER INFORMATION: PCR primer

<400> SEQUENCE: 26

```
ctctcatatg ctgttttggc ggatgagag                                        29
```

<210> SEQ ID NO 27
<211> LENGTH: 33
<212> TYPE: DNA
<213> ORGANISM: Artificial sequence
<220> FEATURE:
<223> OTHER INFORMATION: PCR primer

<400> SEQUENCE: 27
ctctcatatg gtgtctcctc taaagattgt agg                          33

<210> SEQ ID NO 28
<211> LENGTH: 30
<212> TYPE: DNA
<213> ORGANISM: Artificial sequence
<220> FEATURE:
<223> OTHER INFORMATION: PCR primer

<400> SEQUENCE: 28
ctctgatatc ctgttttggc ggatgagaga                              30

<210> SEQ ID NO 29
<211> LENGTH: 35
<212> TYPE: DNA
<213> ORGANISM: Artificial sequence
<220> FEATURE:
<223> OTHER INFORMATION: PCR primer

<400> SEQUENCE: 29
ctctgatatc tctcctctaa agattgtagg aaatg                        35

<210> SEQ ID NO 30
<211> LENGTH: 1401
<212> TYPE: DNA
<213> ORGANISM: Corynebacterium glutamicum

<400> SEQUENCE: 30

| | |
|---|---|
| atgaataggg gtgtgagttg gacagttgat atccctaaag aagttctccc tgatttgcca | 60 |
| ccattgccag aaggcatgca gcagcagttc gaggacacca tttcccgtga cgctaagcag | 120 |
| caacctacgt gggatcgtgc acaggcagaa aacgtgcgca agatccttga gtcggttcct | 180 |
| ccaatcgttg ttgcccctga ggtacttgag ctgaagcaga agcttgctga tgttgctaac | 240 |
| ggtaaggcct tcctcttgca gggtggtgac tgtgcggaaa ctttcgagtc aaacaccgag | 300 |
| ccgcacattc gcgccaacgt aaagactctg ctgcagatgg cagttgtttt gacctacggt | 360 |
| gcatccactc ccgtgatcaa gatggctcgt attgctggtc agtacgcaaa gcctcgctct | 420 |
| tctgatttgg atggaaatgg tctgccaaac taccgtggcg atatcgtcaa cggtgtggag | 480 |
| gcaacccctg aggctcgtcg ccacgatcct gcccgcatga tccgtgctta cgctaacgct | 540 |
| tctgctgcga tgaacttggt gcgcgcgctc accagctctg gcaccgctga tctttaccgt | 600 |
| ctcagcgagt ggaaccgcga gttcgttgcg aactccccag ctggtgcacg ctacgaggct | 660 |
| cttgctcgtg agatcgactc cggtctgcgc ttcatggaag catgtggcgt gtccgatgag | 720 |
| tccctgcgcg ctgcagatat ttactgctcc cacgaggcac ttctcgtgga ttacgagcgc | 780 |
| tccatgctgc gtcttgcaac cgatgaggaa ggcaacgagg aactttacga tctttcagct | 840 |
| caccagctgt ggatcggcga gcgcacccgc ggtatggatg atttccatgt gaacttcgca | 900 |
| tccatgatct ctaacccaat cggcatcaag attggtcctg gtatcacccc tgaagaggct | 960 |
| gttgcatacg ctgacaagct cgatccgaac ttcgagcctg gccgtttgac catcgttgct | 1020 |
| cgcatgggcc acgacaaggt tcgctccgta cttcctggtg ttatccaggc tgttgaggca | 1080 |
| tccggacaca aggttatttg gcagtccgat ccgatgcacg gcaataccct caccgcatcc | 1140 |
| aatggctaca agaccgtca cttcgacaag gttatcgatg aggtccaggg cttcttcgag | 1200 |
| gtccaccgcg cattgggcac ccacccaggc ggaatccaca ttgagttcac tggtgaagat | 1260 |

```
gtcaccgagt gcctcggtgg cgctgaagac atcaccgatg ttgatctgcc aggccgctac    1320
gagtccgcat gcgatcctcg cctgaacact cagcagtctt tggagttggc tttcctcgtt    1380
gcagaaatgc tgcgtaatta a                                              1401
```

<210> SEQ ID NO 31
<211> LENGTH: 306
<212> TYPE: DNA
<213> ORGANISM: Corynebacterium glutamicum

<400> SEQUENCE: 31

```
atgactaatg caggtgacaa cttcgagatc aggatgcctt ctggcacgga tgacccattg      60
tccgatgcgg agatccaaaa gtatcgcgag gagatcaacc gcttggaccg cgaaatcctc     120
gatgcggtga acgtcgcac gaagatttcc caaaccatcg aaaaacacg catgagctcg       180 ggcggaacac gtctcgtgca cacccgagaa gtagcaatca tcaaccagtt ccgtgaagag     240
atcggcgagg aaggccctgc cctcgctgga attttgctgc gcatgggacg cggaaagctc     300
ggataa                                                                306
```

<210> SEQ ID NO 32
<211> LENGTH: 28
<212> TYPE: DNA
<213> ORGANISM: Artificial sequence
<220> FEATURE:
<223> OTHER INFORMATION: PCR primer

<400> SEQUENCE: 32

```
ctctcatatg aatagggtg tgagttgg                                         28
```

<210> SEQ ID NO 33
<211> LENGTH: 35
<212> TYPE: DNA
<213> ORGANISM: Artificial sequence
<220> FEATURE:
<223> OTHER INFORMATION: PCR primer

<400> SEQUENCE: 33

```
ctctcatatg ttaattacgc agcatttctg caacg                                35
```

<210> SEQ ID NO 34
<211> LENGTH: 31
<212> TYPE: DNA
<213> ORGANISM: Artificial sequence
<220> FEATURE:
<223> OTHER INFORMATION: PCR primer

<400> SEQUENCE: 34

```
ctctcatatg actaatgcag gtgacaactt c                                    31
```

<210> SEQ ID NO 35
<211> LENGTH: 28
<212> TYPE: DNA
<213> ORGANISM: Artificial sequence
<220> FEATURE:
<223> OTHER INFORMATION: PCR primer

<400> SEQUENCE: 35

```
ctctcatatg ttatccgagc tttccgcg                                        28
```

<210> SEQ ID NO 36
<211> LENGTH: 1371
<212> TYPE: DNA
<213> ORGANISM: Pantoea agglomerans

<400> SEQUENCE: 36

```
atgaactatc ctgccgagcc tttccgcatt aaaagtgttg aaaccgtatc aatgatctca      60
cgcgatgagc gtgttaaaaa aatgcaagaa gcgggctata acacgttttt actgaattca     120
aaggatatct acatcgatct gctgacagac agcggtacaa atgccatgag tgacaagcag     180
tgggcaggga tgatgattgg tgatgaagcc tacgcaggca gtgaaaactt ctaccatctc     240
gaaaaaacgg tgaaagagtt gtttggtttc aaacacatcg ttccaaccca ccagggacgc     300
ggggcggaaa acctgctctc gcagctggcc attaagcccg tcaatatgt cgcaggaaat     360
atgtacttta caacaacccg cttccatcag gaaaaaaatg cgcaacctt tgtggatatt     420
gtccgcgatg aagcacatga cgccagcctg aatctcccct ttaaaggtaa tattgacctg     480
aataaattag cgacgctcat taagaaaaa ggcgccgaga acatcgccta tatctgcctt     540
gcggtcaccg tgaatctggc gggtgggcag cctgtttcaa tggcgaatat gcgtgccgta     600
catgaaatgg ccagcacgta tggcattaag atctattacg atgctacccg ttgcgttgaa     660
aatgccatt ttatcaaaga gcaggaggcg ggctacgaga acgtcagtat caaagatatc     720
gtgcatgaaa tgttcagcta tgccgatggg tgcaccatga gcgtaaaaa agattgtctg     780
gtgaatatcg gcggcttctt gtgtatgaac gatgaggaga tgttctcagc ggcaaaagag     840
ttggttgtcg tttatgaagg tatgccgtca tacggcgggc tggccggtcg ggatatggaa     900
gcaatggcta ttgggctacg tgaagccatg cagtatgaat atattgaaca tcgggtcaaa     960
caggtgcgct atctgggcga taaactccgt gaagccggcg tacccattgt tgaaccgacg    1020
ggcggacatg cggtatttct tgatgctcgt cgtttctgtc cacacctgac gcaggatcag    1080
ttccctgcgc agagcctggc agccagcatc tatatgaaaa ccggcgtgcg aagtatggaa    1140
cgtggaattg tttccgccgg tcgtagcaag gaaacggggg agaaccatag ccccaaactg    1200
gagacggtac gtctcactat tccacgccgt gtttacactt acgcgcacat ggatgttatt    1260
gccgatggca tcattaaact gtaccagcat aaagaagata ttcgtggtct gacgtttgtt    1320
tacgaaccta acaacttcg cttctttact gcgcgttttg actttattta a               1371
```

<210> SEQ ID NO 37
<211> LENGTH: 26
<212> TYPE: DNA
<213> ORGANISM: Artificial sequence
<220> FEATURE:
<223> OTHER INFORMATION: PCR primer

<400> SEQUENCE: 37

```
ctctcatatg aactatcctg ccgagc                                           26
```

<210> SEQ ID NO 38
<211> LENGTH: 38
<212> TYPE: DNA
<213> ORGANISM: Artificial sequence
<220> FEATURE:
<223> OTHER INFORMATION: PCR primer

<400> SEQUENCE: 38

```
ctctcatatg ttaaataaag tcaaaacgcg cagtaaag                              38
```

<210> SEQ ID NO 39
<211> LENGTH: 1371
<212> TYPE: DNA
<213> ORGANISM: Citrobacter braakii

<400> SEQUENCE: 39

```
atgaattatc cggcagaacc cttccgtatt aaaagcgttg aaactgtatc tatgatcccg        60
cgtgatgaac gccttaagaa aatgcaggaa gcgggataca atactttcct gttaaattcg       120
aaagatattt atattgacct gctgacagac agtggcacca acgcaatgag tgacaagcag       180
tgggccggca tgatgatggg tgatgaagcc tacgcgggca gcgaaaactt ctatcatctg       240
gaaagaaccg tgcaggaact gttcggcttt aaacatattg ttcctactca ccaggggcgc       300
ggcgcagaaa acctgttatc gcagctggca attaaaccgg gcaatatgt tgccgggaat       360 atgtatttca ctaccacccg ttatcaccag gaaaaaaatg gtgcggtgtt tgtcgatatc       420
gttcgtgatg aagcgcacga tgccggtctg aatattgctt ttaaaggtga tatcgatctt       480
aaaaaattac aaaagctgat tgatgaaaaa ggcgccgaga atattgccta tatttgcctg       540
gcagtcacgg ttaacctcgc aggcgggcag ccggtctcca tggctaacat gcgcgcggtg       600
cgtgaactga ctgcagcaca tggcattaaa gtgttctacg acgctacccg ctgcgtagaa       660
aacgcctact ttatcaaaga gcaagagcag ggctttgaga caagagcat cgcagagatc       720 gtgcatgaga tgttcagcta cgccgacggt tgtaccatga gtggtaaaaa agactgtctg       780
gtgaatatcg gcggcttcct gtgcatgaac gatgacgaaa tgttctcttc tgccaaagag       840
ttagtcgttg tttacgaagg tatgccatct tacggcggcc tggccggacg cgacatggaa       900
gccatggcga ttggtctgcg cgaagccatg cagtatgagt acatcgagca ccgcgtgaag       960
caggttcgct atctgggcga caagctgaaa gccgctggtg taccgattgt tgaaccggtg      1020
ggcggtcatg cggtattcct cgatgcgcgt cgcttctgtg agcatctgac gcaggacgag      1080
ttcccggcgc aaagcctggc tgccagtatc tatgtggaaa ccggcgtacg tagtatggag      1140
cgcggaatta tctctgcggg ccgtaataac gtgaccggtg aacaccacag gccgaaactg      1200
gaaaccgtgc gtctgactat tccacgccgc gtttatactt acgcgcatat ggatgtggtg      1260
gctgacggta ttattaaact ttaccagcac aaagaagata ttcgcgggct gaagtttatt      1320
tacgagccga agcagctccg tttctttact gcacgctttg actatatcta a               1371
```

<210> SEQ ID NO 40
<211> LENGTH: 27
<212> TYPE: DNA
<213> ORGANISM: Artificial sequence
<220> FEATURE:
<223> OTHER INFORMATION: PCR primer

<400> SEQUENCE: 40

```
ctcttcatga attatccggc agaaccc                                           27
```

<210> SEQ ID NO 41
<211> LENGTH: 33
<212> TYPE: DNA
<213> ORGANISM: Artificial sequence
<220> FEATURE:
<223> OTHER INFORMATION: PCR primer

<400> SEQUENCE: 41

```
ctcttcatga ttagatatag tcaaagcgtg cag                                    33
```

<210> SEQ ID NO 42
<211> LENGTH: 1374
<212> TYPE: DNA
<213> ORGANISM: Desulfitobacterium hafniense

<400> SEQUENCE: 42

-continued

```
atgaaaacct atcctgcaga accttttaga attaaagtcg tggaacccgt tcggtcgatg      60
aagcgggcag aacgtgaagc ggccatgaaa gaagcaggct acaacacttt tttgctgaag     120
agtgaggatg tctatattga tctgctcaca gattccggca ctactgccat gagcgataaa     180
caatgggccg gtatgatgat cggtgatgaa gcctatgccg ggagcaggaa tttcctgcac     240
ctggatcggg tggttaaaga atattatggc ttcaagcaca tggtccctac tcatcaagga     300 cggggggcg aaaacctgct ctcccggctg atgattaaac ccggggatta tgtgcccggc      360
aatatgtatt ttaccaccac aagataccat caggaagcca acggagctac cttcagagat     420
attatcattg tgaagcccca tgactcagcc aaccggcatc ctttcaaagg aaatatcgat     480
ctcaggaaac tccagacctt aatcgatgaa gtaggcgcgg agaagattcc ttacatctgc     540
cttgccgtta ctgtcaatct ggccggagga cagcccgttt ctctggaaaa catgaaggcg     600
gtccatgagc ttgcccacaa acacggcatc aaggtgtttt ttgacgctac ccgctgtgtg     660
gagaacgctt acttcatcaa gaagcgggaa gcagactacc aggacaagac catcaaagaa     720
attctcttgg agatgatgag ctatgccgac ggagccacca tgtcgggtaa aaaagattgt     780
atggtcaata tcggcggttt tctggccatg aatgatgatg aattgttcct cagggttaaa     840
gaactggtgg tggtctttga aggaatgcct tcttacggcg gcatggccgg ccgggacatg     900
gaagccatgg ccatcgggat tacgaatcg gtggattatg cttatattga acaccgtgtg     960
gagcaggtgg cctatcttgc cgatcagctt ttagcggcgg gggttcccat tgtggaaccg    1020
gtgggcggcc atgccgtctt ccttgatgcc agacggtttt tgccccacct tgagcaggac    1080
cacttcccgg cacaggctct ggccgcccaa ttatatatag aatccggggt acgctctatg    1140
gaaagaggaa tcatctcccg cggacgtgat cttaaaacag gggaaaaccg ccatcctaaa    1200
ctggagctgg taaggctgac gattccccgc cgggtttata cttacgctca tatggacatc    1260
gtggccagag cggttattga gctttaccag caaagggaga ccatcaaagg gcttaaattt    1320
gtttacgaac cggaaatgct tcgtttcttc accgccagat tgaacacat ttga            1374
```

<210> SEQ ID NO 43
<211> LENGTH: 33
<212> TYPE: DNA
<213> ORGANISM: Artificial sequence
<220> FEATURE:
<223> OTHER INFORMATION: PCR primer

<400> SEQUENCE: 43
ctctgatatc atgaaaacct atcctgcaga acc                                    33

<210> SEQ ID NO 44
<211> LENGTH: 33
<212> TYPE: DNA
<213> ORGANISM: Artificial sequence
<220> FEATURE:
<223> OTHER INFORMATION: PCR primer

<400> SEQUENCE: 44
ctctgatatc tcaaatgtgt tcaaatctgg cgg                                    33

<210> SEQ ID NO 45
<211> LENGTH: 1419
<212> TYPE: DNA
<213> ORGANISM: Chloroflexus aurantiacus

<400> SEQUENCE: 45

```
atgcaggaac aagactaccc ccgtacaatg gggcaacaat tcggtcggcg gtcgtgggcc      60
gagccgtgga agatcaagat ggttgagccg ctgcgcgtga ccagccgggc cgaacgcgag     120
gcggcgctga aggctgccgg ttacaacacg tttctgctgc gttctgaaga tgtctatatc     180
gatctgctta ccgatagtgg taccaatgcc atgagcgacc ggcaatgggc agccctgatg     240
atgggcgacg aggcatacgc cgggagccgc agtttttatc gcctggaagc aactgtccaa     300
caggtgtatg gctaccgcca cattattccc acccatcagg ggcggggcgc cgagcatctg     360
atcagtcagg tcgctatccg ccgtgggcag tatgttcccg gcaatatgta tttcacaacc     420
acccgcctgc accaggagct ggccggtggc atctttgttg atgtgattat tgacgaagcg     480
cacgatcccc aaagccagta tccgtttaaa ggcaacgtcg atctcgacaa actacaggcg     540
ctgattgata aggttggccc gcaacagatt gcctatatca gtctggccgg taccgtcaac     600
atggctggtg ggcagccggt cagtatggct aacgtccgtg ccttacgcgc attatgtgat     660
cggtacgggt tgcgcatctt tctcgattcc acacgcttgg ttgagaatgc cttttttcatc     720 aaagaacgtg aacccggcta tgccgaacaa agaatcgccg cgattgtccg cgagttttgc     780
agttacaccg atggcgcatg gatgagcgca aagaaggacg cgctggtgaa catcggtggc     840
tggttagcgc tcaacgatga tcaactcgcc gatgaagccc gcaatctggt ggtggtgtac     900
gaagggttgc acacctacgg cggcatggcc gggcgtgata tggaggcgct ggcggtcggg     960
attgaggagt cgctgcaaga ggattacatc cgtgcccgca tcggtcaggt gcgctacctc    1020
ggcgaactgc tcctcgactg ggacatcccc atcgtagttc cgattggcgg tcacgcgatc    1080
tttctggatg cacgccggtt ctatccgcac ctgccgcaag acctcttccc tgcccagacc    1140
ctggccgccg agttgtacct cgattcaggg gtgcgggcta tggaacgcgg tattgccagc    1200 gccgacgcg atcccaagac cgggcagaac tactatccca aactggaatt aacccggctg    1260
accatcccgc gccgtgttta tactcaggcc cacatggatg ttgtggccga gtcggtgaag    1320
gcagtgtacg atcaacgtca tcaggcccgt ggcctgcgga tggtctacga accacggtac    1380
ctccgcttct tccaggcccg gtttgaaccg gtggaatga                            1419

<210> SEQ ID NO 46
<211> LENGTH: 27
<212> TYPE: DNA
<213> ORGANISM: Artificial sequence
<220> FEATURE:
<223> OTHER INFORMATION: PCR primer

<400> SEQUENCE: 46
ctctcatatg caggaacaag actaccc                                         27

<210> SEQ ID NO 47
<211> LENGTH: 30
<212> TYPE: DNA
<213> ORGANISM: Artificial sequence
<220> FEATURE:
<223> OTHER INFORMATION: PCR primer

<400> SEQUENCE: 47
ctctcatatg tcattccacc ggttcaaacc                                      30

<210> SEQ ID NO 48
<211> LENGTH: 1404
<212> TYPE: DNA
<213> ORGANISM: Nostoc punctiforme

<400> SEQUENCE: 48
```

```
atgaccgatg ccaagcaaac ttctccgcgc cgccgtcgct cttgggcaga gccatataaa    60
attaaggtgg ttgagccatt aaaaattact actcgcgctg aacgcgaaca ggcgatcgca    120
caagcgggtt acaatacttt tctactacgt tctgaagatg tctatattga tttgctcact    180
gatagcggca cttcagccat gagcgattat cagtgggcag gatgatgct gggtgatgaa    240 gcttatgccg gcagcaaaaa tttttacaat ttagaagcaa gtatccaaaa gtattacggc    300
tatcgccata ttgtacctac tcaccaaggg cgtggtgcag aaaatattct ttctcaaata    360
ctgatcaaac caggagacta catacctggc aatatgtatt tcaccacaac caggttgcat    420
caggagttag ctggcggcac ttttgtcgat gtgattattg atgaagccca cgatgcccaa    480
tcactgcatc catttaaggg taatgtagac ttacaaaagc ttacagacct aattgagcga    540 gttgggcag aacgtattcc ctatattagc gttgccggaa ccgtgaatat ggctggcgga    600
cagccgattt ctatggctaa cctgcgggcg gtacatcagt tagcccaaac ctacggtatc    660
cgcattattc ttgatgccac ccgcgctgtg gaaaacgctc actttatcca acagcgagag    720
gaggattatt ccagccaagc gatcgctacc atcttacgcg aattttgctc ctataccgac    780
ggttgcacca tgagcggtaa gaaggatgca ctggttaaca tcggcggttg gctggctctt    840
aatgactata atctttacga agaagcacgt aacttaatag taatttatga aggtctacat    900
acttacggtg gtatggctgg ccgggacatg gaagctatgg cacgaggtat agaagaatca    960
gttcaagacg atcatattcg tgcccgtgtc ggtcaggttg agtatcttgg acaaaagctt    1020
ttagattggg gtattccaat tgttgtgccg attggcggtc atgccattta tttagatgcc    1080
aaacgctttt taccacaaat tccccaagac caatttccgg cacaacgtct agcagcagaa    1140
ctgtatctag aggcaggcat tcgggcaatg gaacggggca tcgtttccgc agggcgcaat    1200
aaagaaacag gcgataatta ttatccagag ttagaattag tccgtttaac tattccacgc    1260
cgtgtttaca ctcaggctca catggatctg actgctgaag cagttgaaga agtttatcat    1320
aatcgcgatc gcctacgcgg actcaaaatg atttatgagc cgaagtatct ccgtttcttt    1380
caagcaagat ttgaattgca gtaa    1404
```

<210> SEQ ID NO 49
<211> LENGTH: 27
<212> TYPE: DNA
<213> ORGANISM: Artificial sequence
<220> FEATURE:
<223> OTHER INFORMATION: PCR primer

<400> SEQUENCE: 49
ctctcatatg accgatgcca agcaaac    27

<210> SEQ ID NO 50
<211> LENGTH: 38
<212> TYPE: DNA
<213> ORGANISM: Artificial sequence
<220> FEATURE:
<223> OTHER INFORMATION: PCR primer

<400> SEQUENCE: 50
ctctcatatg ttactgcaat tcaaatcttg cttgaaag    38

<210> SEQ ID NO 51
<211> LENGTH: 1380
<212> TYPE: DNA
<213> ORGANISM: Treponema denticola

<400> SEQUENCE: 51

```
atggatatta aaaattatcc tgcggaacct tttagaatta aggttgtaga aactgttaag      60
atgatcgata aggatcaaag agcaaaggtt gccaagaag ccggttataa taccttcctt     120
attaattcgg aagatgttta tatcgacctt cttaccgact ccggaacaaa cgccatgagc    180
gataaacaat gggccggaat gatgatagga gatgaagcct atgccggaag ccgcaacttt    240
catcacttgg aagaaacggt tcaagagatt ttcggcttta agcatcttgt gccgacccat    300
caaggccgcg gtgccgaaaa ccttctttca aggatagcca ttaaacccgg tcaatatgta    360
cccggcaaca tgtattttac cactaccaga taccatcagg aagcaaacgg cggtatcttc    420
gtggatatca taaacgatga tgctcatgat gcaggcaaaa atgttccttt taaaggcgac    480
atcgacttga acaagcttga aaagcttata aagaaaagg gagccgaaaa tatagcctat    540
gtatgtttgg ctgttacggt aaaccttgca ggcggtcagc ccgtttctat gaagaacatg    600
aaggccgtcc gtgagcttac aaaaaagcac ggcatcaagg tattctacga tgcaaccccgc   660
tgtgtagaaa acgcctactt tatcaaagaa caagaagccg ttatgccga caagtctatc    720
aaagaaatcg taagagaaat gttcagctat gcagacggat gtaccatgag cggtaaaaaa    780
gactgtatcg taaacatcgg aggcttcctc tgtatgaacg atgaagatct tttccaagct    840
gcaaaagaat tcgttgttgt atttgaaggt atgccttcat acggcggtat ggcaggacgc    900
gatatggaag ctatggctat cggtctaaaa gaagctctcc agtttgaata catcgaacac    960
cgaatcaagc aggtccgcta tttaggcgac aagctcttgg aagccggagt tcctattatt   1020
gagcccgtag aggacatgc agtatttctt gatgcaagac gcttctgtcc tcatcttaag   1080
caaaccgaat ttcccgcaca ggccctagcc gcagagcttt atatcgaatc gggagttaga   1140
agtatggaac gcggtatcgt ttctgcagga cgcgatccca aaacaaggga aaaccacgta   1200
ccaaagcttg aaacagtccg cttaacaatt ccgcgccgtg tttatacata taaacacatg   1260
gacattgtag cagatgccgt tattaaattg tacaaacaca aggaagttat aaaaggatta   1320
aagttcgttt acgaacctaa acaactccgc ttctttacgg cacgctttga gcatatctaa   1380
```

<210> SEQ ID NO 52
<211> LENGTH: 35
<212> TYPE: DNA
<213> ORGANISM: Artificial sequence
<220> FEATURE:
<223> OTHER INFORMATION: PCR primer

<400> SEQUENCE: 52

```
ctctcatatg gatattaaaa attatcctgc ggaac                                35
```

<210> SEQ ID NO 53
<211> LENGTH: 32
<212> TYPE: DNA
<213> ORGANISM: Artificial sequence
<220> FEATURE:
<223> OTHER INFORMATION: PCR primer

<400> SEQUENCE: 53

```
ctctcatatg ttagatatgc tcaaagcgtg cc                                   32
```

<210> SEQ ID NO 54
<211> LENGTH: 30
<212> TYPE: DNA
<213> ORGANISM: Artificial sequence
<220> FEATURE:
<223> OTHER INFORMATION: PCR primer

<400> SEQUENCE: 54
ctctctgcag tgaagtgcgt gtaaacgcac                                30

<210> SEQ ID NO 55
<211> LENGTH: 41
<212> TYPE: DNA
<213> ORGANISM: Artificial sequence
<220> FEATURE:
<223> OTHER INFORMATION: PCR primer

<400> SEQUENCE: 55
gcttagctag ttggtcggtt gcaatgattt gcacgttgga g                  41

<210> SEQ ID NO 56
<211> LENGTH: 20
<212> TYPE: DNA
<213> ORGANISM: Artificial sequence
<220> FEATURE:
<223> OTHER INFORMATION: PCR primer

<400> SEQUENCE: 56
aaccgaccaa ctagctaagc                                          20

<210> SEQ ID NO 57
<211> LENGTH: 30
<212> TYPE: DNA
<213> ORGANISM: Artificial sequence
<220> FEATURE:
<223> OTHER INFORMATION: PCR primer

<400> SEQUENCE: 57
ctcttctaga aattactcct gccatggcag                               30

<210> SEQ ID NO 58
<211> LENGTH: 29
<212> TYPE: DNA
<213> ORGANISM: Artificial sequence
<220> FEATURE:
<223> OTHER INFORMATION: PCR primer

<400> SEQUENCE: 58
ctcttctaga tacgtcctaa acacccgac                                29

<210> SEQ ID NO 59
<211> LENGTH: 40
<212> TYPE: DNA
<213> ORGANISM: Artificial sequence
<220> FEATURE:
<223> OTHER INFORMATION: PCR primer

<400> SEQUENCE: 59
gaccaaccat tgctgacttg cgtatccata gtcaggcttc                    40

<210> SEQ ID NO 60
<211> LENGTH: 20
<212> TYPE: DNA
<213> ORGANISM: Artificial sequence
<220> FEATURE:
<223> OTHER INFORMATION: PCR primer

<400> SEQUENCE: 60
caagtcagca atggttggtc                                          20

<210> SEQ ID NO 61

<211> LENGTH: 30
<212> TYPE: DNA
<213> ORGANISM: Artificial sequence
<220> FEATURE:
<223> OTHER INFORMATION: PCR primer

<400> SEQUENCE: 61

| ctcttctaga tgatcagtac caagggtgag | 30 |
|---|---|

<210> SEQ ID NO 62
<211> LENGTH: 1443
<212> TYPE: DNA
<213> ORGANISM: Corynebacterium efficiens

<400> SEQUENCE: 62

| gtgcagcaca ctccttttca tgtaaaaggt ctcaggcgtg ctatgaatag gggtgtgagt | 60 |
|---|---|
| tggacagttg atatcccaa ggaagttctc ccggatctgc cgcccctgcc cgagggcatg | 120 |
| aacgagcagt tccaggacac catcgcccgt gacgccaagc agcagcccac ctgggaccgt | 180 |
| gcccaggccg acaacgtgcg ccgtatcctc gaatcggttc ctccgatcgt ggtggcccct | 240 |
| gaggtcatcg agctgaagaa gaagctcgca gatgtggcca acggcaaggc attcctgctc | 300 |
| cagggtggtg actgcgccga gaccttcgag tccaataccg agcccatat ccgggccaat | 360 |
| atcaagactc tcctccagat ggccgtggtg ctcacctatg gtgcctccac acccgtcatc | 420 |
| aagatggccc gtatcgccgg ccagtacgcc aagccacggt ccgccgatct ggatgccaac | 480 |
| ggtctgccaa actaccgcgg tgacatcgtc aacggtgtgg aagccacacc ggaggcacgc | 540 |
| cggcatgacc ccgcgcgcat gatccgcgcc tacgccaact cctccgccgc catgaacctg | 600 |
| gtgcgtgccc tgaccagctc cgggaccgcc aacctctacc gcctcagtga ctggaaccgc | 660 |
| gagttcgtcg ccaactcccc cgccggtgcg cgctatgagg cgctcgcccg agagatcgac | 720 |
| tccggtctgc gcttcatgga ggcctgtggc gtgtccgatg aatccctgcg caccgcggag | 780 |
| atctactgct cccacgaggc tctcctcgtg gattatgagc gctccatgct gcgcctgggt | 840 |
| gaggatgaaa acggtgagca ggccctctat gatctctctg cacaccagct gtggatcggt | 900 |
| gagcgcaccc gtggcatgga tgatttccac gtcaatttcg ccgccatgat cgccaacccg | 960 |
| gtgggcatca agatcggccc gggcatcaca cccgaggaag ccgtggccta tgccgataaa | 1020 |
| ctggacccca acttcgaacc gggtcgcctc accatggttg cccgcatggg tcatgacaag | 1080 |
| gtccgttccg tgctccccgg tgtcatccag gctgtggagg cttccggtca aaggtcatc | 1140 |
| tggcagtccg accccatgca cggcaacacc ttcaccgcct ccaatggtta caagacccgt | 1200 |
| cacttcgaca aggtcatcga tgaggtgcag ggattcttcg aggtccaccg cgcactgggc | 1260 |
| acccaccccgg gtggtatcca cattgaattc accggtgagg atgtcaccga atgccttggc | 1320 |
| ggtgcagagg acatcaccga cgtggatctg ccgggccgtt atgagtccgc ctgcgacccc | 1380 |
| cgtctgaaca cccagcagtc ccttgaactg tccttcctcg tggcggagat gctgcgtaat | 1440 |
| tag | 1443 |

<210> SEQ ID NO 63
<211> LENGTH: 1395
<212> TYPE: DNA
<213> ORGANISM: Mycobacterium smegmatis

<400> SEQUENCE: 63

| gtgaactgga ccgtcgacat ccccatcgac cagctaccgc ctttgccgcc gctgtccgac | 60 |
|---|---|
| gagcttcggc aacggctgga ttcggcactg gccaagccgg ctgtccagca gcccagctgg | 120 |

```
gaccccgatg ccgccaaggc catgcgcacg gtcctggaga gcgtgccgcc ggtcaccgtg    180
ccgtcggaga tcgagaagct caagggtctg ctcgccgacg tcgcgcaggg caaggcgttc    240
ctgctgcagg gcggtgactg cgccgagacc ttcgtcgaca acaccgaacc gcacatccgc    300
gccaacatcc gcacgctgct gcagatggcg gtggtgctga cctacggcgc gagcatgccg    360
gtggtgaagg ttgcccgcat cgccgggcag tacgccaagc cgcggtcctc cgacgtcgac    420
gcgctggggc tcaagtccta ccgcggcgac atgatcaacg gtttcgcccc cgatgccgcg    480
gccccgcgaac atgatccgtc gcgtctggtg cgcgcgtacg ccaacgcgag cgcggcgatg    540
aacctgatgc gtgcgctgac ctcgtcgggg ctggcgtcgc tgcatctggt gcacgagtgg    600
aaccgcgaat tcgtccgcac gtcgcccgcc ggagcgcgtt acgaggcgct ggccggtgag    660
atcgaccgcg gcctgaactt catgtcggcc tgcggtgtcg ccgaccgcaa cctgcagacc    720
gccgagatct tcgcgagcca cgaggccctg gtgctcgact acgagcgcgc gatgctgcgc    780
ctgtccaacc cggccgagac cgacggtgcg gccaagctgt acgaccagtc ggcgcactac    840
ctgtggatcg gtgagcgcac acggcaactc gacggcgcgc acgtcgcgtt cgccgaggtg    900
atcgccaacc cgatcggcgt caagctcggt ccgaccacca cgccggaact cgccgtcgag    960
tacgtcgagc gccttgaccc gaacaacgaa ccgggccggc tgacgctcgt gacccgcatg   1020
ggcaacaaca aggtgcgcga cctgctgccg ccgatcatcg agaaggtgca ggccaccgga   1080
catcaggtga tctggcagtg cgacccgatg cacggcaaca cccatgagtc gtccacgggg   1140
tacaagacca ggcacttcga ccgcatcgtc gacgaggtgc agggcttttt cgaggtgcac   1200
cacgcgctgg gcacgcatcc cggcggcatc cacgtcgaga tcaccggcga aaacgtcacc   1260
gaatgtctcg gtggggcaca ggacatttcg gattccgacc tggccggccg ctacgagacc   1320
gcgtgcgatc cgcgcctcaa cacccagcag agcctgaaac tcgcgttctt ggtcgcggag   1380
atgctccgcg attag                                                    1395

<210> SEQ ID NO 64
<211> LENGTH: 1386
<212> TYPE: DNA
<213> ORGANISM: Rhodococcus opacus

<400> SEQUENCE: 64
gtgaactgga ctgtcgacgt gccgatcgac cgcttgcccg aactcccgcc gctgcccacc     60
gagatgcgtg agcgcctcga cgcagcgctg gccaagcccg ctgcccagca gccgcaatgg    120
cccgaaggtc aggccgccgc gatgcggacc gtcctcgaga gcgtgccccc catcacggtg    180
gccagcgagg tcgtggccct gcaggagaag ctcgcccagg tcgcgcgcgg cgaggcgttc    240
ctcctccagg gcggtgactg cgccgagacg ttcgcggaca acaccgagcc gcacatcaag    300
ggcaacatcc gcaccctgct gcagatggcc gtcgtcctga cgtacggcgc gagcctgccc    360
gtcgtcaagg tcgcgcgcat cgccggtcag tacgcgaagc cgcggtcgtc caacgtcgac    420
gccctgggcc tgcagtccta ccgcggcgac atgatcaact ccctcgtcgc ggacgaggcc    480
gtgcgcgccc acgacccgtc gcggctcgtg cgggcgtacg cgaacgccag cgccgcgatg    540
aacctggtcc gcgcactcac cggcgcgggc atggccgacc tgcacaaggt gcacgactgg    600
aaccgcgaat tcgtgtcgtc gtcgccggcc ggggcccggt acgaggcgct cgccgcggag    660
atcgaccgcg gcctgcagtt catgaacgcc tgcggtgtca ccgatcccag cctgcatcac    720
gcccagatct tcgccagcca cgaggcgctc gtcctcgact acgagcgcgc gatgctgcgc    780
```

```
ctcgacaacg acgacgacca cgccaagctg tacgacctgt ccgcccactt cctgtggatc    840
ggcgaccgca cccgtcagct cgacggagcg cacatcgcgt cgccgaact cgtgtcgaac     900 ccgatcggcc tgaagatcgg accgagcacc accccggaga tggcggtcga atacgtcgaa    960
cgcctcgacc ccaccaacaa gccgggccgg ctcacgctga tctcgcgcat gggcaacaac    1020
aaggtgcgcg acctgctgcc gcccatcatc gagaaggtgc aggccaccgg tcaccaggtg    1080
atctggcagt gcgacccgat gcacggcaac acgcacgagg cgtccaccgg ctacaagacc    1140
cgccacttcg accgcatcgt cgacgaggtc cagggattct tcgaggtcca caatggtctc    1200
ggcacctacc cgggcggcat ccacgtcgaa ctcaccggtg agaacgtcac cgaatgcctc    1260
ggcggcgcgc aggacatctc cgacctcgac ctgtccggtc gctacgagac ggcgtgcgac    1320
ccccgcctca cacccagca gtcgctggaa ctggcgttcc tcgtcgcgga gatgctgcgc    1380
ggctga                                                               1386
```

<210> SEQ ID NO 65
<211> LENGTH: 303
<212> TYPE: DNA
<213> ORGANISM: Corynebacterium efficiens

<400> SEQUENCE: 65

```
atgactaatg cggatgagaa cttcgaaatc agaatgccgt caggcaccga cgacccactc    60
tctgatgcgg agatccagaa gtatcgtgag gaaatcgacc gcctcaaccg ggagatcctc    120
gatgcggtga acgtcgcac caagattgcg caggctatcg gcaagacccg catggaatcc    180
ggtggcaccc gtctggtgca cacgcgtgag gtggccatca tcaaccagtt ccgtgatgag    240
atcggtgagg agggcccggc cctggctgcg atcctcctgc gtatgggtcg gggcaagctg    300
tag                                                                  303
```

<210> SEQ ID NO 66
<211> LENGTH: 267
<212> TYPE: DNA
<213> ORGANISM: Mycobacterium smegmatis

<400> SEQUENCE: 66

```
atgcctgaga ccatcgatgc cgtgcctgag atcgatgacc tgcgtcgtga gatcgacgaa    60
ctcgacgcca ccatcatcgc cgccatccag cggcgcaccg aagtgtcgaa gaccatcggt    120
aaagcacgca tggcatcggg cggtacccgc ctggtccaca gccgtgagat gaaggtcatc    180
gagcgctaca tcgacgcgct cggccccgag ggcaaggacc tcgcgatgct gttgctgcgc    240
ctcggccgcg gccgcctcgg gtactag                                        267
```

<210> SEQ ID NO 67
<211> LENGTH: 297
<212> TYPE: DNA
<213> ORGANISM: Rhodococcus opacus

<400> SEQUENCE: 67

```
atgagcactc agaccgtcgc ttcagccgcc aaggaaaccg ctgtgcccac cagcgaggcc    60
gagatcgagg ttctccgcca ggagatcgac aagctcgacg ccgagattct cgccgcgatc    120
aagcgccgcg ccgaggtctc gcagctcatc gggcgcaccc ggatggcgtc cggcggtccc    180
cgcctcgtcc acagccgtga gatgaaggtg ctcgagcggt tcaacgagct gggccaggaa    240
ggccacacgc tcgccatgct gctgctgcgt ctcgggcgcg ccgcctcgg tcactga       297
```

US 9,328,361 B2

CORYNEFORM BACTERIUM TRANSFORMANT AND PROCESS FOR PRODUCING PHENOL USING THE SAME

TECHNICAL FIELD

The present invention relates to a technique for producing phenol. In more detail, the present invention relates to a coryneform bacterium transformant constructed by specific gene recombination and thereby provided with a phenol producing function, and relates to an efficient phenol producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

However, production of biophenol using renewable resources is less productive as compared to production of lactic acid or ethanol because the metabolic reaction from a raw material saccharide consists of a great many steps. In addition, for the reasons that produced phenol inhibits bacterial proliferation and that phenol is cytotoxic, industrial production of phenol has been considered to be impossible.

Important use of phenol is phenol resins. A phenol resin, which is produced by addition condensation of phenol and aldehyde, is one of the oldest plastics, and with its properties including excellent heat resistance and durability, is used for various purposes, such as an alternative automotive material to metal, a semiconductor seal material, and a circuit board even today. Due to extremely high reactivity of phenol and aldehyde as raw materials and to the complicated three-dimensional network structure of resulting phenol resin polymers, precise structural designing and development into nanomaterials thereof had been considered difficult and so had been application to high-value-added use. However, in recent years, the theory of physical-properties of polymers and the simulation thereof have rapidly developed, and therefore it has gradually become possible to create highly functional materials from phenol resins by refining the network structure. Under the circumstances, the phenol resin production in Japan is also increasing year by year.

The currently employed industrial production process of phenol (cumene process) is a typical energy-consumptive process in the chemical industry using petroleum-derived benzene and propylene as raw materials, and requiring great amounts of solvent and thermal energy. Therefore, in the light of global environment conservation and greenhouse gas reduction, there is an urgent need to develop an environment-conscious, energy saving process that allows production of phenol from renewable resources and can reduce carbon dioxide emissions and waste products, that is, to establish biophenol production technologies.

No phenol-producing bacteria in nature have been reported so far.

Examples of known phenol producing technologies using recombinant bacteria include Non Patent Literature 1. In the process of Non Patent Literature 1, a strain constructed by transferring a tpl gene which is derived from *Pantoea agglomerans* and encodes tyrosine phenol-lyase into a solvent-resistant strain *Pseudomonas putida* S12, and a strain constructed by transferring an aroF-1 gene which is derived from a *Pseudomonas putida* S12 strain and encodes DAHP (3-deoxy-D-arabino-heptulosonate 7-phosphate) synthase into a *Pseudomonas putida* S12 strain were created and used. In addition, from among strains constructed by transferring an aroF-1 gene which is derived from *Pseudomonas putida* S12 strain and encodes DAHP synthase into *Pseudomonas putida* S12 strains, strains resistant to m-fluoro-DL-phenylalanine, which is an analogue of phenylalanine or tyrosine, were selected and used. Further, from among the selected strains, strains resistant to m-fluoro-L-tyrosine were selected and used. These strains were subjected to a fed-batch culture under aerobic conditions using glucose as an only carbon source for phenol production in the disclosed technology.

However, the process of Non Patent Literature 1 does not have a practically sufficient phenol productivity.

CITATION LIST

Non Patent Literature

[NPL 1] Applied and Environmental Microbiology, Vol. 71, 2005, 8221-8227

SUMMARY OF INVENTION

Technical Problem

An object of the present invention is to provide a microorganism capable of efficiently producing phenol from a saccharide, and a process for efficiently producing phenol from a saccharide using the microorganism.

Solution to Problem

The present inventors have wholeheartedly carried out investigations in order to achieve the object described above and obtained the following findings.
(i) A coryneform bacterium has high resistance to phenol.
(ii) A transformant constructed by transferring a tyrosine phenol-lyase gene into a coryneform bacterium efficiently produces phenol.
(iii) The transformant further efficiently produces phenol in the case where the prephenate dehydratase gene and/or the phenol 2-monooxygenase gene on the chromosome of the coryneform bacterium as the host has a disruption or deletion.
(iv) The transformant further efficiently produces phenol in the case where the DAHP synthetase gene and/or the chorismate mutase gene is expressed at a higher level as compared to the gene expression level before transformation.
(v) The transformant has a higher phenol productivity when proliferation is substantially inhibited in a reaction mixture under reducing conditions than when proliferation is allowed in an aerobic reaction mixture.

The present invention, which has been completed based on the above-mentioned findings, provides the following transformant and process for producing phenol.
[1] A phenol-producing transformant constructed by transferring a gene which encodes an enzyme having tyrosine phenol-lyase activity into a coryneform bacterium as a host.
[2] The transformant of the above [1], wherein the gene which encodes an enzyme having tyrosine phenol-lyase activity is a gene derived from *Pantoea agglomerans*, a gene derived from *Citrobacter braakii*, a gene derived from *Desulfitobacterium hafniense*, a gene derived from *Chloroflexus aurantiacus*, a gene derived from *Nostoc punctiforme*, or a gene derived from *Treponema denticola*.

[3] The transformant of the above [1], wherein the gene which encodes an enzyme having tyrosine phenol-lyase activity is the DNA of the following (a) or (b).
(a) a DNA consisting of the base sequence of SEQ ID NO: 36, a DNA consisting of the base sequence of SEQ ID NO: 39, a DNA consisting of the base sequence of SEQ ID NO: 42, a DNA consisting of the base sequence of SEQ ID NO: 45, a DNA consisting of the base sequence of SEQ ID NO: 48, or a DNA consisting of the base sequence of SEQ ID NO: 51
(b) a DNA which hybridizes to a DNA consisting of a complementary base sequence of any of the DNAs of (a) under stringent conditions and which encodes a polypeptide having tyrosine phenol-lyase activity
[4] The transformant of any one of the above [1] to [3], wherein the following gene (c) and/or gene (d) on the chromosome of the coryneform bacterium as the host has a disruption or deletion.
(c) a gene which encodes an enzyme having prephenate dehydratase activity
(d) a gene which encodes an enzyme having phenol 2-monooxygenase activity
[5] The transformant of any one of the above [1] to [4], wherein the following metabolic gene (e) and/or metabolic gene (f) of the coryneform bacterium as the host is highly expressed.
(e) a gene which encodes an enzyme having DAHP (3-deoxy-D-arabino-heptulosonate 7-phosphate) synthase activity
(f) a gene which encodes an enzyme having chorismate mutase activity
[6] The transformant of any one of the above [1] to [5], wherein the coryneform bacterium as the host is *Corynebacterium glutamicum*.
[7] The transformant of the above [6], wherein the *Corynebacterium glutamicum* as the host is *Corynebacterium glutamicum* R (FERM BP-18976), ATCC13032, or ATCC13869.
[8] The transformant of the above [6], wherein the following gene (c) and/or gene (d) on the chromosome of *Corynebacterium glutamicum* R (FERM BP-18976), ATCC13032, or ATCC13869 as the host *Corynebacterium glutamicum* has a disruption or deletion.
(c) a gene which encodes an enzyme having prephenate dehydratase activity
(d) a gene which encodes an enzyme having phenol 2-monooxygenase activity
[9] The transformant of the above [6] or [8], wherein the following metabolic gene (e) and/or metabolic gene (f) of *Corynebacterium glutamicum* R (FERM BP-18976), ATCC13032, or ATCC13869 as the host *Corynebacterium glutamicum* is highly expressed.
(e) a gene which encodes an enzyme having DAHP (3-deoxy-D-arabino-heptulosonate 7-phosphate) synthase activity
(f) a gene which encodes an enzyme having chorismate mutase activity
[10] A *Corynebacterium glutamicum* transformant PHE7 (Accession Number: NITE BP-976).
[11] A process for producing phenol, which comprises a step of reacting the transformant of any one of the above [1] to [10] in a reaction mixture containing a saccharide under reducing conditions, and a step of collecting phenol from the reaction mixture.
[12] The process of the above [11], wherein the transformant does not substantially proliferate in the reaction step.
[13] The process of the above [11] or [12], wherein the oxidation-reduction potential of the reaction mixture under reducing conditions is −200 mV to −500 mV.

[14] The process of any one of the above [11] to [13], wherein the saccharide is selected from a group consisting of glucose, fructose, mannose, xylose, arabinose, galactose, sucrose, maltose, lactose, cellobiose, trehalose, and mannitol.

Advantageous Effects of Invention

With the use of the transformant of the present invention, phenol can be produced from a saccharide more efficiently than with the use of a known transformant.

Generally, growth of microorganisms is inhibited by a solvent, such as a phenol, because of its cytotoxicity, and therefore phenol production with the use of microorganisms was difficult. According to the process of the present invention, however, phenol production with the use of microorganisms can be achieved with a practically sufficient efficiency.

DESCRIPTION OF EMBODIMENTS

Figure 1A:
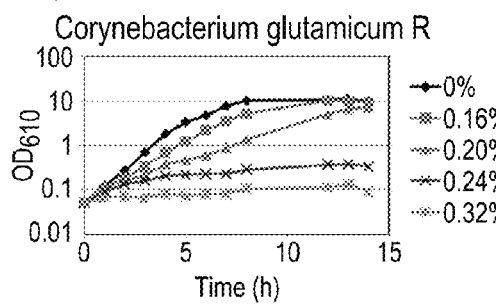
FIG. 1 shows the influence of phenol on proliferation of various microorganisms under aerobic conditions.
Figure 1B:
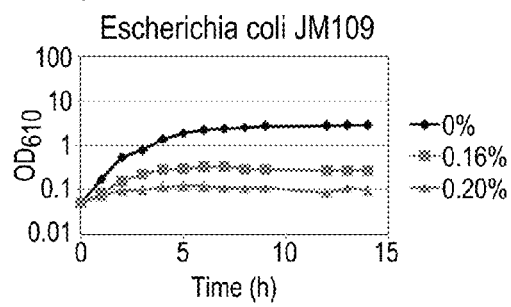
Figure 1C:
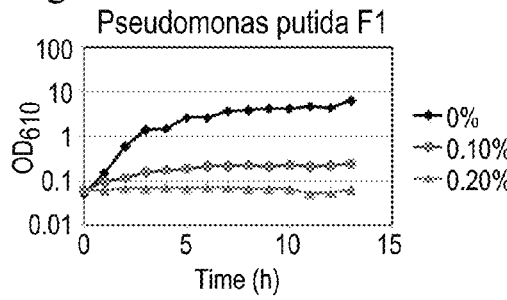
Figure 1D:
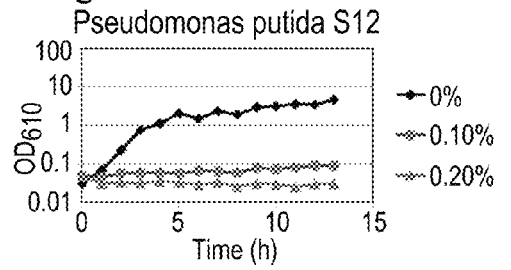

Hereinafter, the present invention will be described in detail.
(I) Phenol-Producing Transformant
The transformant of the present invention capable of producing phenol is a transformant constructed by transferring a gene which encodes an enzyme having tyrosine phenol-lyase activity into a coryneform bacterium as a host.
Host
The coryneform bacteria is a group of microorganisms defined in Bargeys Manual of Determinative Bacteriology, Vol. 8, 599 (1974), and members thereof are not particularly limited as long as they proliferate under normal aerobic conditions. The specific examples include *Corynebacterium*, *Brevibacterium*, *Arthrobacter*, *Mycobacterium* and *Micrococcus*. Among the coryneform bacteria, *Corynebacterium* is preferred.
Examples of the *Corynebacterium* include *Corynebacterium glutamicum*, *Corynebacterium efficiens*, *Corynebacterium ammoniagenes*, *Corynebacterium halotolerance*, and *Corynebacterium alkanolyticum*. Inter alia, *Corynebacterium glutamicum* is preferred for safety and high phenol production. Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, strains R (FERM P-18976), ATCC13032, and ATCC13869 are preferred.
According to molecular biological classification, names of species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium*

*flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the cryneform group of bacteria", Fermentation and industry, 45: 944-963 (1987)).

*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.

Examples of the *Brevibacterium* include *Brevibacterium ammoniagenes* (for example, ATCC6872).

Examples of the *Arthrobacter* include *Arthrobacter globiformis* (for example, ATCC8010, ATCC4336, ATCC21056, ATCC31250, ATCC31738 and ATCC35698).

Examples of the *Mycobacterium* include *Mycobacterium bovis* (for example, ATCC19210 and ATCC27289).

Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve phenol productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, preferred is a disruptant of *Corynebacterium glutamicum*, especially the R (FERM P-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1.

Tyrosine Phenol-lyase Gene (tpl)

Tyrosine phenol-lyase is an enzyme that catalyzes the following two reactions.

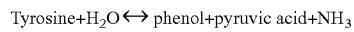
Tyrosine+$H_2O$ ↔ phenol+pyruvic acid+$NH_3$

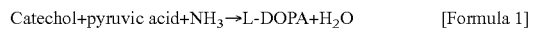
Catechol+pyruvic acid+$NH_3$→L-DOPA+$H_2O$ [Formula 1]

The gene which encodes an enzyme having tyrosine phenol-lyase activity may be of any origin without particular limitation, and preferred are a gene derived from *Pantoea agglomerans*, a gene derived from *Citrobacter braakii*, a gene derived from *Desulfitobacterium hafniense*, a gene derived from *Chloroflexus aurantiacus*, a gene derived from *Nostoc punctiforme*, or a gene derived from *Treponema denticola*. Inter alia, preferred is a gene derived from *Pantoea agglomerans*, *Citrobacter braakii*, or *Desulfitobacterium hafniense*, and more preferred is a gene derived from *Citrobacter braakii*.

Examples of the tyrosine phenol-lyase gene derived from *Pantoea agglomerans* include the DNA consisting of the base sequence of SEQ ID NO: 36, examples of the tyrosine phenol-lyase gene derived from *Citrobacter braakii* include the DNA consisting of the base sequence of SEQ ID NO: 39, examples of the tyrosine phenol-lyase gene derived from *Desulfitobacterium hafniense* include the DNA consisting of the base sequence of SEQ ID NO: 42, examples of the tyrosine phenol-lyase gene derived from *Chloroflexus aurantiacus* include the DNA consisting of the base sequence of SEQ ID NO: 45, examples of the tyrosine phenol-lyase gene derived from *Nostoc punctiforme* include the DNA consisting of the base sequence of SEQ ID NO: 48, and examples of the tyrosine phenol-lyase gene derived from *Treponema denticola* include the DNA consisting of the base sequence of SEQ ID NO: 51.

In the present invention, a DNA which hybridizes to a DNA consisting of a complementary base sequence of the base sequence of SEQ ID NO: 36, 39, 42, 45, 48, or 51 under stringent conditions and which encodes a polypeptide having tyrosine phenol-lyase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

The tyrosine phenol-lyase activity can be determined by the method described later in Example 3.

In the present invention, a DNA consisting of a base sequence which has 90% or more, preferably 95% or more, more preferably 98% or more homology with the base sequence of SEQ ID NO: 36, 39, 42, 45, 48, or 51 and which encodes a polypeptide having tyrosine phenol-lyase activity can also be used.

The base sequence homology was calculated using GENETYX Ver. 8 (made by Genetyx).

The homolog of the DNA consisting of the base sequence of SEQ ID NO: 36, 39, 42, 45, 48, or 51 can be selected from a DNA library of a different species by, for example, PCR or hybridization using a primer or a probe designed based on these base sequences, according to a conventional method, and as a result, a DNA which encodes a polypeptide having tyrosine phenol-lyase activity can be obtained with a high probability.

Construction of Vector for Transformation

The PCR-amplified DNA which encodes tyrosine phenol-lyase may be cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum/Escherichia coli* shuttle vectors for cloning, controlled gene expression, and promoter probing. Gene, 102: 93-98 (1991)), etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*), and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for coryneform bacteria is electroporation, which can be performed by a known method (Kurusu, Y. et al., Electroporation-transformation system for Coryneform bacteria by auxotrophic complementation., Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of a microorganism. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In the coryneform bacterium as a host, the gene which encodes an enzyme having prephenate dehydratase activity (pheA) and/or the gene which encodes an enzyme having phenol 2-monooxygenase activity (poxF), both existing on the chromosome, preferably has a disruption or deletion for further efficient phenol production. It is more preferred that both of pheA and poxF have a disruption or deletion.

Replacement of a gene on the chromosome with the corresponding gene having an disruption or deletion can be achieved by creating a gene with deletion mutation for not allowing production of a normally functioning enzyme protein, and transforming a bacterium with a DNA comprising the mutated gene for recombination in which the gene on the chromosome and the mutated gene are exchanged. An enzyme protein encoded by a gene having a disruption or deletion, even when produced, has a conformation different from that of the wild type, and has no or reduced function. The gene deletion or gene disruption by way of gene substitution through the use of such homologous recombination has already been established, and examples thereof include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

Specifically, by the method described in Example 2, a coryneform bacterium in which the prephenate dehydratase gene or the phenol 2-monooxygenase gene is disrupted or deleted can be obtained.

High Expression of Metabolic Gene

It is preferred that the DAHP (3-deoxy-D-arabino-heptulosonate 7-phosphate) synthase gene (aroG) and/or the chorismate mutase gene (csm) is expressed at a higher level in the coryneform bacterium as a host as compared with the original level in the host, i.e., the level in the wild type host. Such high expression is achieved by transformation via gene transfer or by increase in the number of copies of the desired gene(s) on the chromosome of the host. It is more preferred that both of aroG and csm are highly expressed.

Regarding the transformation, the DAHP synthetase gene and the chorismate mutase gene may be the same or substantially same as those of the host, or of different types. Preferably, the DAHP synthetase gene and/or the chorismate mutase gene may be the same or substantially same as those of the host.

Examples of the DAHP synthetase gene derived from *Corynebacterium glutamicum* include the DNA consisting of the base sequence of SEQ ID NO: 30, and examples of the chorismate mutase gene derived from *Corynebacterium glutamicum* include the DNA consisting of the base sequence of SEQ ID NO: 31.

Examples of the DAHP synthetase gene derived from different types of coryneform bacteria include a gene derived from *Corynebacterium efficiens* (SEQ ID NO: 62, DNA Data Bank of Japan: CE2073), a gene derived from *Mycobacterium smegmatis* (SEQ ID NO: 63, DNA Data Bank of Japan: MSMEG_4244), and a gene derived from *Rhodococcus opacus* (SEQ ID NO: 64, DNA Data Bank of Japan: ROP_08400). Examples of the chorismate mutase gene derived from different types of coryneform bacteria include a gene derived from *Corynebacterium efficiens* (SEQ ID NO: 65, DNA Data Bank of Japan: CE0929), a gene derived from *Mycobacterium smegmatis* (SEQ ID NO: 66, DNA Data Bank of Japan: MSMEG_5536), and a gene derived from *Rhodococcus opacus* (SEQ ID NO: 67, DNA Data Bank of Japan: ROP_56380).

Regarding the DAHP synthetase gene or the chorismate mutase gene, examples of the "substantially same gene" include a DNA which encodes a polypeptide having 90% or more, preferably 95% or more, and more preferably 98% or more homology with the amino acid sequence of a polypeptide encoded by the gene, and having a DAHP synthetase activity or a chorismate mutase activity. Regarding the DAHP synthetase gene or the chorismate mutase gene, examples of the "substantially same gene" include a DNA which has 90% or more, preferably 95% or more, and more preferably 98% or more homology with the gene, and which encodes a polypeptide having a DAHP synthetase activity or a chorismate mutase activity.

The DAHP synthetase activity can be determined by the reaction of phosphoenolpyruvic acid and erythrose-4-phosphate as substrates followed by quantification of produced 3-deoxy-D-arabino-heptulosonate 7-phosphate (DAHP) by a chromogenic method with the use of thiobarbituric acid (Appl. Environ. Microbial., 74: 5497-5503 (2008)).

The chorismate mutase activity can be determined by the reaction of chorismic acid as a substrate followed by conversion of the produced prephenate to phenylpyruvate with the use of 0.67 N (final concentration) hydrochloric acid (about 10-minute incubation) and by subsequent concentration determination based on the increase in absorbance at 320 nm (generation of phenylpyruvic acid) (Microbiology, 155, 3382-3391 (2009)).

To increase the number of copies of the DAHP synthetase gene or the chorismate mutase gene on the chromosome of the host, multiple copies of the gene may be transferred onto the chromosomal DNA. To transfer multiple copies of a gene onto the chromosomal DNA of a microorganism, homologous recombination (Experiments in Molecular Genetics, Cold Spring Harbor Lab. (1972)) may be performed using, as a target, a sequence that exists as multiple copies on the chromosomal DNA. As the sequence that exists as multiple copies on the chromosomal DNA, a repetitive DNA or an inverted repeat that exists at the end of a transposon may be used. Also, as disclosed in JP 02-109985 A, it is feasible to transfer multiple copies of the desired gene with a transposon onto the chromosomal DNA. Further, by a method using Mu phage (JP 02-109985 A), the desired gene may be transferred onto a host chromosome.

Substitution of an expression control sequence, such as a promoter, of the DAHP synthetase gene and/or the chorismate mutase gene with a stronger one can also increase the expression of such a gene. For example, a tac promoter, a lac promoter, a trc promoter, a trp promoter, etc. are known as a strong promoter. Further, as disclosed in WO 00/18935, it is also feasible to alter a promoter to a stronger one by substitution of a few bases in the promoter region of the gene. Examples of the evaluation method of the strength of a promoter and examples of such a promoter are described in a paper by Goldstein et al. "Prokaryotic promoters in biotechnology". Biotechnol. Annu. Rev., 1995, 1, 105-128, etc. Substitution of an expression control sequence can be performed in a similar way to the gene substitution with the use of a temperature sensitive plasmid, for example.

Further, it is known that substitution of a spacer between a ribosomal binding site (RBS) and an initiator codon, in particular substitution of a few nucleotides in a sequence immediately upstream of the initiator codon has a great influence on the efficiency of mRNA translation. Therefore, the alteration thereof can improve the amount of translation.

Examples of the method for the above-mentioned gene substitution include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

(II) Process for Producing Phenol

Phenol can be produced by a process comprising a step of reacting the above-described transformant of the present invention in a reaction mixture containing a saccharide under reducing conditions, and a step of collecting phenol from the reaction mixture.

Proliferation of Microorganism

Before the reaction, the transformant is preferably cultured and proliferated under aerobic conditions at about 25 to 38° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium containing a saccharide at a concentration in the above-mentioned range can be used.

Reaction Mixture

The reaction mixture may be a natural or synthetic medium containing a carbon source, a nitrogen source, inorganic salts, other nutritional substances, etc.

As the carbon source, a saccharide is used. Examples of the saccharide include monosaccharides such as glucose, fructose, mannose, xylose, arabinose, and galactose; disaccharides such as sucrose, maltose, lactose, cellobiose, xylobiose, and trehalose; polysaccharides such as starch; and molasses. Inter alia, a monosaccharide is preferred, and glucose is more preferred.

As the carbon source, besides saccharides, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

These carbon sources may be used alone or as a mixture of two or more thereof.

The concentration of the saccharide in the reaction mixture is preferably about 1 to 20 w/v %, more preferably about 2 to 10 w/v %, and still more preferably about 2 to 5 w/v %.

The total concentration of the carbon sources including the saccharide in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the reaction mixture varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the reaction mixture varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the reaction mixture is preferably about 6 to 8.

Specific examples of the preferable culture medium for coryneform bacteria include A medium and BT medium as described above. Such a culture medium containing a saccharide at a concentration in the above-mentioned range can be used.

Reaction Conditions

The reaction temperature, that is, the temperature at which the transformant lives is preferably about 20 to 50° C., and more preferably about 25 to 47° C. When the temperature is in the above range, phenol can be efficiently produced.

The reaction period is preferably about 1 to 7 days, and more preferably about 1 to 3 days.

The culture may be a batch process, a fed-batch process, or a continuous process. Inter alia, a batch process is preferred.

The reaction may be performed under aerobic conditions or reducing conditions.

Reducing Conditions

Under reducing conditions, a coryneform bacterium does not substantially proliferate and can further efficiently produce phenol.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Collection of Phenol

Through the culture performed in the above manner, phenol is produced in the reaction mixture. Phenol can be collected by collecting the reaction mixture, and it is also feasible to isolate phenol from the reaction mixture by a known method. Examples of such a known method include distillation, the membrane permeation method, and the organic solvent extraction method.

EXAMPLES

Hereinafter, the present invention will be illustrated in more detail by Examples, but is not limited thereto.

Example 1

Test for Suitability as a Host for Phenol Production; Influence of Phenol on *Corynebacterium glutamicum* and Other Bacterial Cells (1) Influence of Phenol on Aerobic Proliferation A growth inhibition test in aerobic culture was performed to examine the influence of phenol on *Corynebacterium glutamicum*, *Escherichia coli*, and *Pseudomonas putida*. *Pseudomonas putida* S12, which was used for the test, is reported to be a solvent-resistant strain. In the report, disclosed is an unparalleled technology using the strain as a host in phenol production.

*Corynebacterium glutamicum* R was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of *Corynebacterium glutamicum* R grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose suspended in 1 L of distilled water) and was aerobically cultured with shaking at 33° C. for 13 hours.

The *Corynebacterium glutamicum* R grown in the above conditions was inoculated into 100 mL of A liquid media in such a way that the initial bacterial cell concentration would be $OD_{610}$=0.05, phenol was added at the same time in such a way that the final concentration would be 0, 0.16, 0.2, 0.24, or 0.32 mM, and aerobic culture was performed with shaking at 33° C. The growth of bacterial cells was determined by absorbance measurement at $OD_{610}$.

*Escherichia coli* JM109 was applied to LB agar medium (1% polypeptone, 0.5% yeast extract, 0.5% NaCl and 1.5% agar) and was left stand in the dark at 37° C. for 15 hours.

An inoculation loop of *Escherichia coli* JM109 was inoculated into a test tube containing 10 mL of LB liquid medium (1% polypeptone, 0.5% yeast extract, and 0.5% NaCl), and aerobic culture was performed with shaking at 37° C. for 13 hours.

*Escherichia coli* JM109 grown in the above conditions was inoculated into 100 mL of LB liquid medium in such a way that the initial bacterial cell concentration would be $OD_{610}$=0.05, phenol was added at the same time in such a way that the final concentration would be 0, 0.16, or 0.20 mM, and aerobic culture was performed with shaking at 37° C. The growth of bacterial cells was determined by absorbance measurement at $OD_{610}$.

*Pseudomonas putida* F1 and S12 were applied to LB agar medium (1% polypeptone, 0.5% yeast extract, 0.5% NaCl and 1.5% agar) and were left stand in the dark at 30° C. for 15 hours.

An inoculation loop of each of *Pseudomonas putida* F1 and S12 was inoculated into a test tube containing 10 mL of LB (+glucose) liquid medium (1% polypeptone, 0.5% yeast extract, 0.5% NaCl and 0.4% glucose), and aerobic culture was performed with shaking at 30° C. for 13 hours.

*Pseudomonas putida* F1 and S12 grown in the above conditions were each inoculated into 100 mL of LB (+glucose) liquid medium in such a way that the initial bacterial cell concentration would be $OD_{610}$=0.05, phenol was added at the same time in such a way that the final concentration would be 0, 0.10, or 0.20 mM, and aerobic culture was performed with shaking at 30° C. The growth of bacterial cells was determined by absorbance measurement at $OD_{610}$. FIG. 1 shows analysis results of the influence of phenol addition on aerobic proliferation. The vertical axis of FIG. 1 indicates $OD_{610}$.

The proliferation of *Escherichia coli* was significantly affected by 0.16% phenol and completely inhibited by 0.20% phenol.

*Pseudomonas putida* F1, and *Pseudomonas putida* S12, which was reported as a solvent-resistant strain, showed a similar tendency, and the proliferation thereof was significantly affected by 0.10% phenol and completely inhibited by 0.20% phenol.

In contrast, the proliferation of *Corynebacterium glutamicum* was hardly affected by 0.16% phenol, which significantly affected the proliferation of *Escherichia coli*. Even in the presence of 0.20% phenol, which completely inhibited the proliferation of *Escherichia coli* and *Pseudomonas putida*, *Corynebacterium glutamicum* showed favorable growth. Further, *Corynebacterium glutamicum* was able to proliferate in the presence of 0.24% phenol.

Thus, it was shown that *Corynebacterium glutamicum* has a higher resistance to phenol as compared with *Escherichia coli* and *Pseudomonas putida*, and is highly suitable as a host in phenol production.

(2) Influence of Phenol on Saccharide Metabolism Under Reducing Conditions

*Corynebacterium glutamicum* R was applied to A agar medium and was left stand in the dark at 33° C. for 20 hours.

An inoculation loop of the *Corynebacterium glutamicum* R grown on a plate as above was inoculated into a test tube containing 10 mL of A liquid medium and was aerobically cultured with shaking at 33° C. for 15 hours.

The *Corynebacterium glutamicum* R grown in the above conditions was inoculated into a 2 L-conical flask containing 500 mL of A liquid medium and was aerobically cultured with shaking at 33° C. for 15 hours.

The bacterial cells cultured and proliferated as above were collected by centrifugation (5,000×g at 4° C. for 15 minutes). The obtained bacterial cells were suspended in BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the concentration of the bacterial cell was 10% (w/v). To 100-mL medium bottles containing 60 mL of the suspension, glucose and phenol were added so as to be 8% and 0, 0.24, 0.38, or 0.46 mM in concentration, respectively, and the reaction was allowed to proceed under reducing conditions (the ORP of the reaction mixture: −450 mV) in a water bath kept at 33° C. with stirring. During the reaction, 2.5 N aqueous ammonia was added with the use of a pH controller (Type: DT-1023 made by Able) to avoid the pH of the reaction mixture falling below 7.0.

Figure 2:
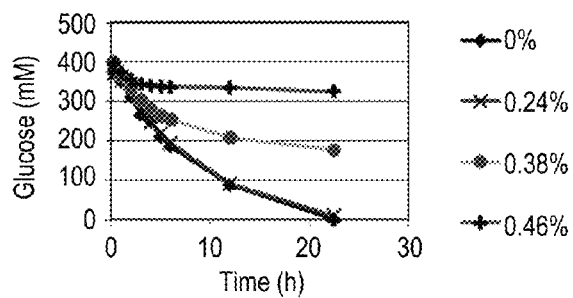
FIG. 2 shows the influence of phenol on the saccharide consumption by *Corynebacterium* under reducing conditions.

FIG. 2 shows the influence of phenol on the saccharide metabolism in *Corynebacterium glutamicum* R under reducing conditions.

Under reducing conditions, even in the presence of 0.24% phenol, which caused proliferation inhibition in aerobic culture, no influence of phenol was observed, and the saccharide consumption was comparable to that in the case free from phenol.

Further, saccharide consumption was observed even in the presence of 0.38% phenol, and was slightly observed even in the presence of 0.46% phenol.

Thus, it was shown that *Corynebacterium glutamicum* has a higher resistance to phenol under reducing conditions as compared with in aerobic culture, and that phenol production using *Corynebacterium glutamicum* as a host under reducing conditions is advantageous as compared with the production under aerobic conditions.

Example 2

Cloning and Expression of Phenol-Producing Genes
(1) Extraction of Chromosomal DNA from Microorganisms To extract chromosomal DNA from *Corynebacterium glutamicum* R (FERM P-18976), the bacterium was inoculated, with the use of a platinum loop, into A medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pantoea agglomerans* NBRC12686, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Citrobacter braakii* ATCC6750, the bacterium was inoculated into Nutrient Broth (made by Becton, Dickinson and Company, BD 234000) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Desulfitobacterium hafniense* Y51, the bacterium was inoculated into MMYP medium (7.8 g of $K_2HPO_4$, 1.2 g of $KH_2PO_4$, 0.5 g of sodium citrate, 0.1 g of $MgSO_4.7H_2O$, 2.0 g of yeast extract, 5.5 g of sodium pyruvate, and 1.0 mg of resazurin sodium salt were dissolved in 1 L of distilled water and the pH was adjusted to 7.2) with the use of a platinum loop, and anaerobically cultured. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Chloroflexus aurantiacus* J-10-fl ATCC 29366, the bacterium was inoculated into *Chloroflexus* medium (0.1 g of nitrilotriacetic acid, 1.0 mL of Micronutrient Solution, 1.0 mL of $FeCl_3$ Solution, 0.06 g of $CaSO_4.2H_2O$, 0.1 g of $MgSO_4.7H_2O$, 0.008 g of NaCl, 0.103 g of $KNO_3$, 0.689 g of $NaNO_3$, 0.111 g of $Na_2HPO_4$, 0.2 g of $NH_4Cl$, 0.5 g of yeast extract, and 0.5 g of glycyl-glycine were dissolved in 1 L of distilled water; Micronutrient Solution: 0.5 mL of $H_2SO_4$, 2.28 g of $MnSO_4.7H_2O$, 0.5 g of $ZnSO_4.7H_2O$, 0.5 g of $H_3BO_3$, 0.025 g of $CuSO_4.2H_2O$, 0.025 g of $Na_2MoO_4.2H_2O$, and 0.045 g of $CoCl_2.6H_2O$ were dissolved in 1 L of distilled water; $FeCl_3$ Solution: 0.2905 g of $FeCl_3$ were dissolved in 1 L of distilled water) with the use of a platinum loop, and cultured at 50° C. with shaking under irradiation from a tungsten lamp. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Nostoc punctiforme* ATCC 29133, the bacterium was inoculated into Blue-green nitrogen-fixing culture-medium (0.04 g of $K_2HPO_4$, 0.075 g of $MgSO_4.7H_2O$, 0.036 g of $CaCl_2.2H_2O$, 6.0 mg of citric acid, 6.0 mg of ferric ammonium citrate, 1.0 mg of EDTA, 0.02 g of $Na_2CO_3$, and 1.0 mL of Trace Metal Mix A5 were dissolved in 1 L of distilled water and the pH was adjusted to 7.1; Trace Metal Mix A5: 2.86 g of $H_3BO_3$, 1.81 g of $MnCl_2.4H_2O$, 0.222 g of $ZnSO_4.7H_2O$, 0.39 g of $Na_2MoO_4.2H_2O$, 0.079 g of $CuSO_4.5H_2O$, and 49.4 mg of $Co(NO_3)_2.6H_2O$ were dissolved in 1 L of distilled water) with the use of a platinum loop, and cultured at 26° C. under light irradiation (2000 to 3000 lux). After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Treponema denticola* JCM 8153 was obtained from the Incorporated Administrative Agency Rikagaku Kenkyusho (RIKEN) (Catalog No. RDB 6217).

(2) Construction of Cloning Vectors
Construction of Cloning Vector pCRB22

A DNA fragment comprising a DNA replication origin sequence of pCASE1, which is a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-ori Sequence Amplification

```
                                        (SEQ ID NO: 3)
(a-1); 5'-AT AGATCT AGAACGTCCGTAGGAGC-3'

(SEQ ID NO: 4)
(b-1); 5'-AT AGATCT GACTTGGTTACGATGGAC-3'
```

Primers (a-1) and (b-1) each have a BglII restriction enzyme site added thereto.
Primers for Cloning Vector pHSG298 Amplification

```
                                        (SEQ ID NO: 5)
(a-2): 5'-AT AGATCT AGGTTTCCCGACTGGAAAG-3'

(SEQ ID NO: 6)
(b-2): 5'-AT AGATCT CGTGCCAGCTGCATTAATGA-3'
```

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.
*)For amplification of the pCASE1-ori sequence, a combination of primers (a-1) and (b-1), and for amplification of the cloning vector pHSG298, a combination of primers (a-2) and (b-2) was used.

PCR Cycle:
Denaturation step: 94° C., 60 seconds
Annealing step: 52° C., 60 seconds
Extension step: 72° C.
pCASE1-ori sequence: 150 seconds
Cloning vector pHSG298: 180 seconds
A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 μL of the about 1.4-kb DNA fragment comprising the pCASE1-ori sequence derived from *Corynebacterium casei*, and 10 μL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

With the use of the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.
Construction of Cloning Vector pCRB11

A DNA fragment comprising a DNA replication origin sequence of pCG1 (JP 57-134500 A), which is a plasmid duplicable in *Corynebacterium glutamicum* (hereinafter abbreviated as pCG1-ori) and a DNA fragment comprising a cloning vector pHSG398 (made by Takara Bio, Inc.) were amplified by the following PCR method.

In the PCR, the following sets of primers were synthesized based on SEQ ID NO: 7 (pCG1-ori sequence) and SEQ ID NO: 8 (cloning vector pHSG398) for cloning of the pCG1-ori sequence and the cloning vector pHSG398, and were used.

Primers for pCG1-ori Sequence Amplification

```
                                        (SEQ ID NO: 9)
(a-3); 5'- AT AGATCT AGCATGGTCGTCACAGAG-3'

(SEQ ID NO: 10)
(b-3); 5'- AT AGATCT GGAACCGTTATCTGCCTATG-3'
```

Primers (a-3) and (b-3) each have a BglII restriction enzyme site added thereto.
Primers for Cloning Vector pHSG398 Amplification

```
                                        (SEQ ID NO: 11)
(a-4); 5'-AT AGATCT GTCGAACGGAAGATCACTTC-3'

(SEQ ID NO: 12)
(b-4); 5'-AT AGATCT AGTTCCACTGAGCGTCAG-3'
```

Primers (a-4) and (b-4) each have a BglII restriction enzyme site added thereto.

As the template DNA, pCG1 (JP 57-134500 A) and cloning vector pHSG398 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the pCG1-ori sequence, a combination of primers (a-3) and (b-3), and for amplification of the cloning vector pHSG398, a combination of primers (a-4) and (b-4) was used.

PCR Cycle:
Denaturation step: 94° C., 60 seconds
Annealing step: 52° C., 60 seconds
Extension step: 72° C.
pCG1-ori sequence: 120 seconds
Cloning vector pHSG398: 150 seconds
A cycle consisting of the above 3 steps was repeated 30 times.

Using 10 μL of the above-produced reaction mixture, 0.8% agarose gel electrophoresis was performed. In the case of the pCG1-ori sequence, an about 1.9-kb DNA fragment was detected. In the case of the cloning vector pHSG398, an about 2.2-kb DNA fragment was detected.

10 μL of the about 1.9-kb DNA fragment comprising the pCG1-ori gene which is derived from the plasmid pCG1, and 10 μL of the about 2.2-kb DNA fragment comprising the cloning vector pHSG398, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid B.

With the use of the Ligation Liquid B, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture and cut with the use of restriction enzyme BglII to confirm the inserted fragment. As a result, in addition to an about 2.2-kb DNA fragment of the cloning vector pHSG398, an about 1.9-kb DNA fragment of the pCG1-ori sequence was confirmed.

The cloning vector comprising the pCG1-ori sequence was named pCRB11.

Construction of Cloning Vector pCRB15

A DNA fragment comprising a cloning vector pCRB11 and a DNA fragment comprising a zeocin resistance gene derived from pSELECT-zeo-mcs (made by Invitrogen Corp.) were amplified by the following PCR method.

In the PCR, the following sets of primers were synthesized based on SEQ ID NO: 13 (pCRB11) and SEQ ID NO: 14 (zeocin resistance gene) for cloning of the cloning vector pCRB11 and the zeocin resistance gene, and were used.

Primers for Cloning Vector pCRB11 Amplification

```
                                    (SEQ ID NO: 15)
(a-5); 5'-AT GATATC CGAAGTGATCTTCCGTTCGA-3'

(SEQ ID NO: 16)
(b-5); 5'-AT GATATC AAGGCAGTTATTGGTGCCCT-3'
```

Primers (a-5) and (b-5) each have an EcoRV restriction enzyme site added thereto.

Primers for Zeocin Resistance Gene Amplification

```
                                    (SEQ ID NO: 17)
(a-6); 5'-AT GATATC TAGCTTATCCTCAGTCCTGC-3'

(SEQ ID NO: 18)
(b-6); 5'-AT GATATC CCATCCACGCTGTTTTGACA-3'
```

Primers (a-6) and (b-6) each have an EcoRV restriction enzyme site added thereto.

As the template DNA, cloning vector pCRB11 and pSELECT-zeo-mcs (made by Invitrogen Corp.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the cloning vector pCRB11 sequence, a combination of primers (a-5) and (b-5), and for amplification of the zeocin resistance gene, a combination of primers (a-6) and (b-6) was used.

PCR Cycle:
Denaturation step: 94° C., 60 seconds
Annealing step: 52° C., 60 seconds
Extension step: 72° C.
pCRB11 sequence: 200 seconds
zeocin resistance gene: 45 seconds
A cycle consisting of the above 3 steps was repeated 30 times.

Using 10 μL of the above-produced reaction mixture, 0.8% agarose gel electrophoresis was performed. In the case of the cloning vector pCRB11 sequence, an about 3.3-kb DNA fragment was detected. In the case of the zeocin resistance gene, an about 0.5-kb DNA fragment was detected.

10 μL of the about 3.3-kb DNA fragment comprising the cloning vector pCRB11 and 10 μL of the about 0.5-kb DNA fragment comprising the zeocin resistance gene which is derived from the plasmid pSELECT-zeo-mcs, both amplified by the above PCR, were each cut with the use of restriction enzyme EcoRV and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid C.

With the use of the Ligation Liquid C, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 25 μg/mL of zeocin.

A growing strain on the culture medium was subjected to liquid culture in the usual manner. Plasmid DNA was extracted from the culture and cut with the use of restriction enzyme EcoRV to confirm the inserted fragment. As a result, in addition to an about 3.3-kb DNA fragment derived from the cloning vector pCRB11, an about 0.5-kb DNA fragment of the zeocin resistance gene was confirmed.

The cloning vector comprising the zeocin resistance gene was named pCRB15.

Construction of Cloning Vector pCRB207

A DNA fragment comprising a promoter sequence of the gapA gene (hereinafter abbreviated as PgapA) encoding the glyceraldehyde-3-phosphate dehydrogenase derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 19 (PgapA sequence) and SEQ ID NO: 20 (terminator sequence) for cloning of the PgapA sequence and the terminator sequence, and were used.

Primers for PgapA Sequence Amplification

```
                                          (SEQ ID NO: 21)
(a-7); 5'-CTCT GTCGAC CCGAAGATCTGAAGATTCCTG-3'

(SEQ ID NO: 22)
(b-7); 5'-CTCT GTCGAC GGATCC CCATGG

TGTGTCTCCTCTAAAGATTGTAGG-3'
```

Primer (a-7) has a SalI restriction enzyme site added thereto, and primer (b-7) has SalI, BamHI, and NcoI restriction enzyme sites added thereto.

Primers for Terminator Sequence Amplification

```
(a-8);
                                          (SEQ ID NO: 23)
5'-CTCT GCATGC CCATGG CTGTTTTGGCGGATGAGAGA-3'

(b-8);
                                          (SEQ ID NO: 24)
5'-CTCT GCATGC TCATGA AAGAGTTTGTAGAAACGCAAAAAGG-3'
```

Primer (a-8) has SphI and NcoI restriction enzyme sites added thereto, and primer (b-8) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the PgapA sequence, a combination of primers (a-7) and (b-7), and for amplification of the terminator sequence, a combination of primers (a-8) and (b-8) was used.

PCR Cycle:
Denaturation step: 94° C., 60 seconds
Annealing step: 52° C., 60 seconds
Extension step: 72° C.
PgapA sequence: 45 seconds
Terminator sequence: 30 seconds
A cycle consisting of the above 3 steps was repeated 30 times.

Using 10 μL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 μL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 μL of the about 0.4-kb DNA fragment comprising the terminator sequence derived from the plasmid pKK223-3, which was amplified by the above PCR, was cut with the use of restriction enzymes NcoI and BspHI, 2 μL of the above cloning vector pCRB206 was cut with the use of restriction enzyme NcoI, and both were processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid E.

With the use of the Ligation Liquid E, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 25 (pCRB207) for cloning of the pCRB207 sequence, and was used.

Primers for pCRB207 Sequence Amplification

```
                                         (SEQ ID NO: 26)
(a-9); 5'-CTCT CATATG CTGTTTTGGCGGATGAGAG-3'

(SEQ ID NO: 27)
(b-9); 5'-CTCT CATATG GTGTCTCCTCTAAAGATTGTAGG-3'
```

Primers (a-9) and (b-9) each have an NdeI restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.
*)For amplification of the pCRB207 sequence, a combination of primers (a-9) and (b-9) was used.

PCR Cycle:

Denaturation step: 94° C., 60 seconds
Annealing step: 52° C., 60 seconds
Extension step: 72° C., 307 seconds A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut with the use of restriction enzyme NdeI and processed at 70° C. for 10 minutes for deactivation of the restriction enzyme. To this, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. This was named Ligation Liquid F.

With the use of the Ligation Liquid F, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme NdeI to confirm the inserted restriction enzyme site.

The cloning vector comprising the PgapA sequence and the rrnBT1T2 terminator sequence was named pCRB209.

Construction of Cloning Vector pCRB210

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 25 (pCRB207) for cloning of the pCRB207 sequence, and was used.

Primers for pCRB207 Sequence Amplification

```
(a-10);
                                         (SEQ ID NO: 28)
5'-CTCT GATATC CTGTTTTGGCGGATGAGAGA-3'

(b-10);
                                         (SEQ ID NO: 29)
5'-CTCT GATATC TCTCCTCTAAAGATTGTAGGAAATG-3'
```

Primers (a-10) and (b-10) each have an EcoRV restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.
*)For amplification of the pCRB207, a combination of primers (a-10) and (b-10) was used.

PCR Cycle:

Denaturation step: 94° C., 60 seconds
Annealing step: 52° C., 60 seconds
Extension step: 72° C., 307 seconds A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut with the use of restriction enzyme EcoRV and processed at 70° C. for 10 minutes for deactivation of the restriction enzyme. To this, 1 µL of T4 DNA ligase 10× buffer solution and 1 unit of T4 DNA ligase (made by Takara SHUZO) were added. Sterile distilled water was added thereto so that the total volume was 10 µL, and the mixture was allowed to react at 15° C. for 3 hours for ligation. This was named Ligation Liquid G.

With the use of the Ligation Liquid G, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme EcoRV to confirm the inserted restriction enzyme site.

The cloning vector comprising the PgapA sequence and the rrnBT1T2 terminator sequence was named pCRB210.

(3) Cloning of Phenol-Producing Genes Cloning of Phenol-Producing Genes Derived from *Corynebacterium glutamicum*

A DNA fragment comprising the aroG gene which encodes DAHP synthase, and a DNA fragment comprising the csm gene which encodes chorismate mutase, both derived from *Corynebacterium glutamicum*, were amplified by the PCR method as described below.

In the PCR, the following sets of primers were synthesized based on SEQ ID NO: 30 (the aroG gene of *Corynebacterium glutamicum*) and SEQ ID NO: 31 (the csm gene of *Corynebacterium glutamicum*) with the use of "394 DNA/RNA Synthesizer" made by Applied Biosystems for cloning of the aroG gene and the csm gene, and were used.

Primers for aroG Gene Amplification

```
(a-11);
                                          (SEQ ID NO: 32)
  5'-CTCT CATATG AATAGGGGTGTGAGTTGG-3'

(b-11);
                                          (SEQ ID NO: 33)
  5'-CTCT CATATG TTAATTACGCAGCATTTCTGCAACG-3'
```

Primers (a-11) and (b-11) each have an NdeI restriction enzyme site added thereto.

Primers for csm Gene Amplification

```
                                          (SEQ ID NO: 34)
(a-12); 5'-CTCT CATATG ACTAATGCAGGTGACAACTTC-3'

(SEQ ID NO: 35)
(b-12); 5'-CTCT CATATG TTATCCGAGCTTTCCGCG-3'
```

Primers (a-12) and (b-12) each have an NdeI restriction enzyme site added thereto.

Cloning of Phenol-Producing Gene Derived from *Pantoea agglomerans*

A DNA fragment comprising the tpl gene which is derived from *Pantoea agglomerans* and which encodes a gene having tyrosine phenol-lyase activity was amplified by the PCR method as described below.

In the PCR, the following set of primers was synthesized based on SEQ ID NO: 36 (the tpl gene of *Pantoea agglomerans*) with the use of "394 DNA/RNA Synthesizer" made by Applied Biosystems for cloning of the tpl gene, and was used.

Primers for tpl Gene Amplification

```
(a-13);
                                          (SEQ ID NO: 37)
  5'-CTCT CATATG AACTATCCTGCCGAGC-3'

(b-13);
                                          (SEQ ID NO: 38)
  5'-CTCT CATATG TTAAATAAAGTCAAAACGCGCAGTAAAG-3'
```

Primers (a-13) and (b-13) each have an NdeI restriction enzyme site added thereto.

Cloning of Phenol-Producing Gene Derived from *Citrobacter braakii*

A DNA fragment comprising the tpl gene which is derived from *Citrobacter braakii* and which encodes a gene having tyrosine phenol-lyase activity was amplified by the PCR method as described below.

In the PCR, the following set of primers was synthesized based on SEQ ID NO: 39 (the tpl gene of *Citrobacter braakii*) with the use of "394 DNA/RNA Synthesizer" made by Applied Biosystems for cloning of the tpl gene, and was used.

Primers for tpl Gene Amplification

```
                                          (SEQ ID NO: 40)
(a-14); 5'-CTCT TCATGA ATTATCCGGCAGAACCC-3'

(SEQ ID NO: 41)
(b-14); 5'-CTCT TCATGA TTAGATATAGTCAAAGCGTGCAG-3'
```

Primers (a-14) and (b-14) each have a BspHI restriction enzyme site added thereto.

Cloning of Phenol-Producing Gene Derived from *Desulfitobacterium hafniense*

A DNA fragment comprising the tpl gene which is derived from *Desulfitobacterium hafniense* and which encodes a gene having tyrosine phenol-lyase activity was amplified by the PCR method as described below.

In the PCR, the following set of primers was synthesized based on SEQ ID NO: 42 (the tpl gene of *Desulfitobacterium hafniense*) with the use of "394 DNA/RNA Synthesizer" made by Applied Biosystems for cloning of the tpl gene, and was used.

Primers for tpl Gene Amplification

```
                                          (SEQ ID NO: 43)
(a-15); 5'-CTCT GATATC ATGAAAACCTATCCTGCAGAACC-3'

(SEQ ID NO: 44)
(b-15); 5'-CTCT GATATC TCAAATGTGTTCAAATCTGGCGG-3'
```

Primers (a-15) and (b-15) each have an EcoRV restriction enzyme site added thereto.

Cloning of Phenol-Producing Gene Derived from *Chloroflexus aurantiacus*

A DNA fragment comprising the tpl gene which is derived from *Chloroflexus aurantiacus* and which encodes a gene having tyrosine phenol-lyase activity was amplified by the PCR method as described below.

In the PCR, the following set of primers was synthesized based on SEQ ID NO: 45 (the tpl gene of *Chloroflexus aurantiacus*) with the use of "394 DNA/RNA Synthesizer" made by Applied Biosystems for cloning of the tpl gene, and was used.

Primers for tpl Gene Amplification

```
                                              (SEQ ID NO: 46)
(a-16); 5'-CTCT CATATG CAGGAACAAGACTACCC-3'

(SEQ ID NO: 47)
(b-16); 5'-CTCT CATATG TCATTCCACCGGTTCAAACC-3'
```

Primers (a-16) and (b-16) each have an NdeI restriction enzyme site added thereto.

Cloning of Phenol-Producing Gene Derived from *Nostoc punctiforme*

A DNA fragment comprising the tpl gene which is derived from *Nostoc punctiforme* and which encodes a gene having tyrosine phenol-lyase activity was amplified by the PCR method as described below.

In the PCR, the following set of primers was synthesized based on SEQ ID NO: 48 (the tpl gene of *Nostoc punctiforme*) with the use of "394 DNA/RNA Synthesizer" made by Applied Biosystems for cloning of the tpl gene, and was used.

Primers for tpl Gene Amplification

```
(a-17);
                                              (SEQ ID NO: 49)
5'-CTCT CATATG ACCGATGCCAAGCAAAC-3'

(b-17);
                                              (SEQ ID NO: 50)
5'-CTCT CATATG TTACTGCAATTCAAATCTTGCTTGAAAG-3'
```

Primers (a-17) and (b-17) each have an NdeI restriction enzyme site added thereto.

Cloning of Phenol-Producing Gene Derived from *Treponema denticola*

A DNA fragment comprising the tpl gene which is derived from *Treponema denticola* and which encodes a gene having tyrosine phenol-lyase activity was amplified by the PCR method as described below.

In the PCR, the following set of primers was synthesized based on SEQ ID NO: 51 (the tpl gene of *Treponema denticola*) with the use of "394 DNA/RNA Synthesizer" made by Applied Biosystems for cloning of the tpl gene, and was used.

Primers for tpl Gene Amplification

```
(a-18);
                                              (SEQ ID NO: 52)
5'-CTCT CATATG GATATTAAAAATTATCCTGCGGAAC-3'

(b-18);
                                              (SEQ ID NO: 53)
5'-CTCT CATATG TTAGATATGCTCAAAGCGTGCC-3'
```

Primers (a-18) and (b-18) each have an NdeI restriction enzyme site added thereto.

As the template DNA for *Corynebacterium glutamicum*, the chromosomal DNA extracted from *Corynebacterium glutamicum* R was used. For *Pantoea agglomerans*, the chromosomal DNA extracted from *Pantoea agglomerans* NBRC12686 obtained from NITE Biological Resource Center (NBRC) was used. For *Citrobacter* braakii, the chromosomal DNA extracted from *Citrobacter braakii* ATCC6750 obtained from American Type Culture Collection (ATCC) was used. For *Desulfitobacterium hafniense*, the chromosomal DNA extracted from *Desulfitobacterium hafniense* Y51 was used. For *Chloroflexus aurantiacus*, the chromosomal DNA extracted from *Chloroflexus aurantiacus* J-10-fl ATCC29366 obtained from American Type Culture Collection (ATCC) was used. For *Nostoc punctiforme*, the chromosomal DNA extracted from *Nostoc punctiforme* ATCC29133 obtained from American Type Culture Collection (ATCC) was used. For *Treponema denticola*, the *Treponema denticola* chromosomal DNA obtained from Japan Collection of Microorganisms (JCM) (catalog No. RDB 6217) was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL, each (final conc.: 1 μM) |
| Sterile distilled water | 25.5 μL |

The above ingredients were mixed, and 50 μL of the reaction mixture was subjected to PCR.
*$^)$For amplification of the aroG gene of *Corynebacterium glutamicum*, a combination of primers (a-11) and (b-11); for amplification of the csm gene of *Corynebacterium glutamicum*, a combination of primers (a-12) and (b-12); for amplification of the tpl gene of *Pantoea agglomerans*, a combination of primers (a-13) and (b-13); for amplification of the tpl gene of *Citrobacter braakii*, a combination of primers (a-14) and (b-14); for amplification of the tpl gene of *Desulfitobacterium hafniense*, a combination of primers (a-15) and (b-15); for amplification of the tpl gene of *Chloroflexus aurantiacus*, a combination of primers (a-16) and (b-16); for amplification of the tpl gene of *Nostoc punctiforme*, a combination of primers (a-17) and (b-17); and for amplification of the tpl gene of *Treponema denticola*, a combination of primers (a-18) and (b-18) were used.

PCR Cycle:
Denaturation step: 94° C., 60 seconds
Annealing step: 52° C., 60 seconds
Extension step: 72° C.

| | |
|---|---|
| *Corynebacterium glutamicum* aroG gene | 84 seconds |
| *Corynebacterium glutamicum* csm gene | 18 seconds |
| *Pantoea agglomerans* tpl gene | 82 seconds |
| *Citrobacter braakii* tpl gene | 82 seconds |
| *Desulfitobacterium hafniense* tpl gene | 82 seconds |
| *Chloroflexus aurantiacus* tpl gene | 85 seconds |
| *Nostoc punctiforme* tpl gene | 84 seconds |
| *Treponema denticola* tpl gene | 83 seconds |

A cycle consisting of the above 3 steps was repeated 30 times.

With the use of 10 μL of the reaction mixture produced above, 0.8% agarose gel electrophoresis was performed. As a result, detected were an about 1.4-kb DNA fragment in the case of the *Corynebacterium glutamicum* aroG gene, an about 0.3-kb DNA fragment in the case of the *Corynebacterium glutamicum* csm gene, an about 1.4-kb DNA fragment in the case of the *Pantoea agglomerans* tpl gene, an about 1.4-kb DNA fragment in the case of the *Citrobacter braakii* tpl gene, an about 1.4-kb DNA fragment in the case of the *Desulfitobacterium hafniense* tpl gene, an about 1.4-kb DNA fragment in the case of the *Chloroflexus aurantiacus* tpl gene, an about 1.4-kb DNA fragment in the case of the *Nostoc punctiforme* tpl gene, and an about 1.4-kb DNA fragment in the case of the *Treponema denticola* tpl gene.

(4) Construction of Phenol-Producing Gene Expression Plasmids Cloning of Phenol-Producing Gene to pCRB207

10 μL of the about 1.4-kb DNA fragment comprising the tpl gene derived from *Citrobacter braakii*, which was amplified by the PCR in the above (3), was cut with the use of restriction enzyme BspHI, 2 μL of the cloning vector pCRB207 comprising promoter PgapA was cut with the use of restriction enzyme NcoI, and each was processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid H.

With the use of the Ligation Liquid H, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 5.1-kb DNA fragment of the plasmid pCRB207, an about 1.4-kb inserted fragment of the tpl gene derived from *Citrobacter braakii* (Ligation Liquid H) was confirmed.

Figure 3:
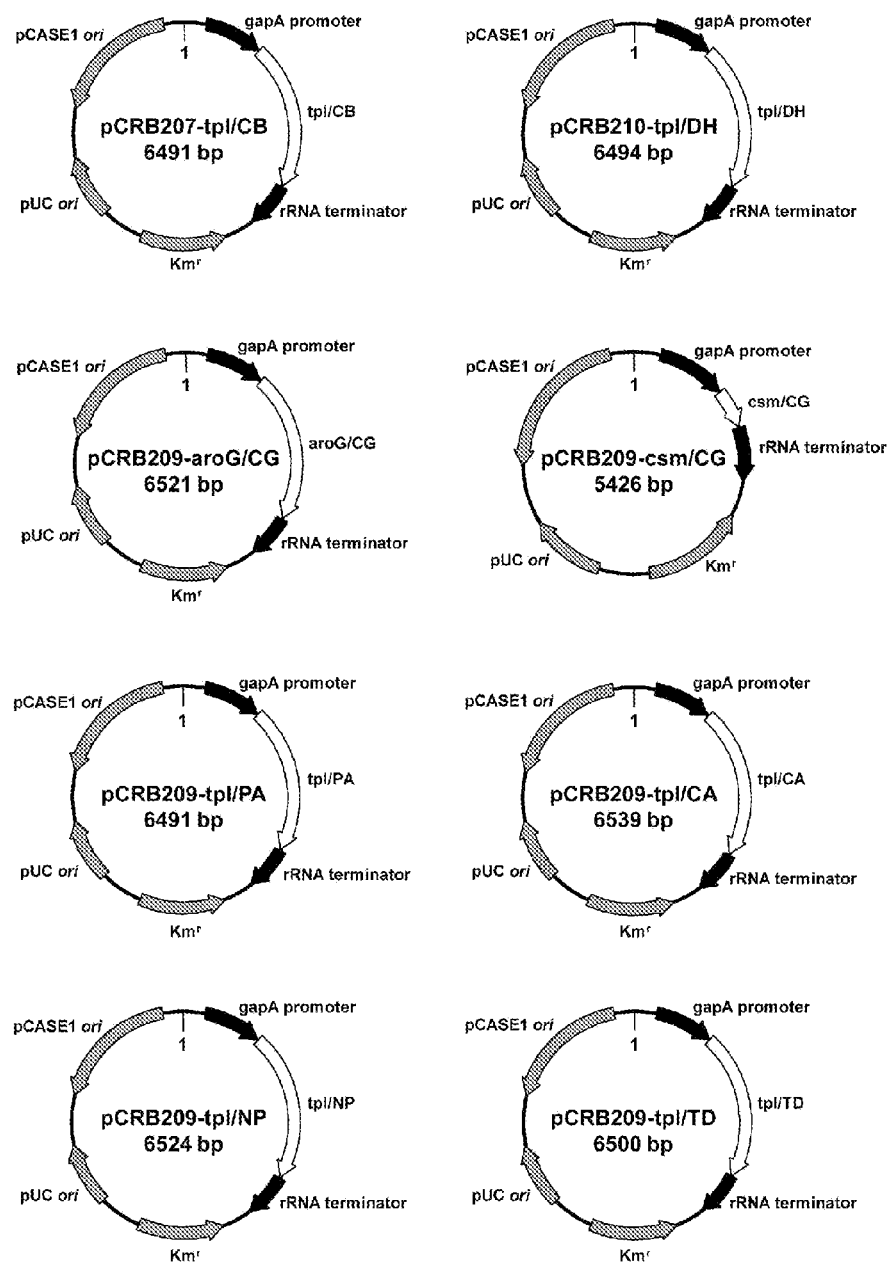
FIG. 3 shows construct of various plasmids used in Examples.

The plasmid comprising the tpl gene derived from *Citrobacter braakii* was named pCRB207-tpl/CB (FIG. 3).

Cloning of Phenol-Producing Genes to pCRB209

10 μL of the about 1.4-kb DNA fragment comprising the aroG gene derived from *Corynebacterium glutamicum*, the about 0.3-kb DNA fragment comprising the csm gene derived from *Corynebacterium glutamicum*, the about 1.4-kb DNA fragment comprising the tpl gene derived from *Pantoea agglomerans*, the about 1.4-kb DNA fragment comprising the tpl gene derived from *Chloroflexus aurantiacus*, the about 1.4-kb DNA fragment comprising the tpl gene derived from *Nostoc punctiforme*, or the about 1.4-kb DNA fragment comprising the tpl gene derived from *Treponema denticola*, each amplified by the PCR in the above (3), and 2 μL of the cloning vector pCRB209 comprising promoter PgapA were cut with the use of restriction enzyme NdeI, and were processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. The resulting liquid was named Ligation Liquids I, J, K, L, M, or N.

With the use of each of the obtained 6 kinds of Ligation Liquids I, J, K, L, M, and N, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme to confirm the inserted fragment. As a result, in addition to an about 5.1-kb DNA fragment of the plasmid pCRB209, confirmed were an about 1.4-kb inserted fragment in the case of the aroG gene derived from *Corynebacterium glutamicum* (Ligation Liquid I), an about 0.3-kb inserted fragment in the case of the csm gene derived from *Corynebacterium glutamicum* (Ligation Liquid J), an about 1.4-kb inserted fragment in the case of the tpl gene derived from *Pantoea agglomerans* (Ligation Liquid K), an about 1.4-kb inserted fragment in the case of the tpl gene derived from *Chloroflexus aurantiacus* (Ligation Liquid L), an about 1.4-kb inserted fragment in the case of the tpl gene derived from *Nostoc punctiforme* (Ligation Liquid M), and an about 1.4-kb inserted fragment in the case of the tpl gene derived from *Treponema denticola* (Ligation Liquid N).

The plasmid comprising the aroG gene derived from *Corynebacterium glutamicum* was named pCRB209-aroG/CG, the plasmid comprising the csm gene derived from *Corynebacterium glutamicum* was named pCRB209-csm/CG, the plasmid comprising the tpl gene derived from *Pantoea agglomerans* was named pCRB209-tpl/PA, the plasmid comprising the tpl gene derived from *Chloroflexus aurantiacus* was named pCRB209-tpl/CA, the plasmid comprising the tpl gene derived from *Nostoc punctiforme* was named pCRB209-tpl/NP, and the plasmid comprising the tpl gene derived from *Treponema denticola* was named pCRB209-tpl/TD (FIG. 3).

Cloning of Phenol-Producing Gene to pCRB210

10 μL of the about 1.4-kb DNA fragment comprising the tpl gene derived from *Desulfitobacterium hafniense*, which was amplified by the PCR in the above (3), and 2 μL of the cloning vector pCRB210 comprising promoter PgapA were each cut with the use of restriction enzyme EcoRV and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid O.

With the use of the Ligation Liquid O, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 5.1-kb DNA fragment of the plasmid pCRB210, an about 1.4-kb inserted fragment of the tpl gene derived from *Desulfitobacterium hafniense* (Ligation Liquid O) was confirmed.

The plasmid comprising the tpl gene derived from *Desulfitobacterium hafniense* was named pCRB210-tpl/DH (FIG. 3).

Cloning of Phenol-Producing Gene to pCRB1

The above plasmid pCRB209-aroG/CG was cut with the use of a restriction enzyme BamHI. After agarose gel electrophoresis, an about 2.4-kb DNA fragment recovered from the agarose gel with the use of QIAquick Gel Extraction Kit (made by QIAGEN), in which fragment a gapA promoter, an aroG gene derived from *Corynebacterium glutamicum*, and a terminator sequence were ligated, and an about 4.1-kb DNA fragment obtained by BamHI digestion of the cloning vector pCRB1, followed by 10 min-treatment at 70° C. for deactivation of BamHI (Nakata, K. et al., Vectors for the genetics engineering of *corynebacteria*; in Saha, B.C. (ed.): Fermentation Biotechnology, ACS Symposium Series 862. Washington, American Chemical Society: 175-191 (2003)) were mixed. To this, 1 μL of T4 DNA ligase 10× buffer solution and 1 unit of T4 DNA ligase (made by Takara Bio, Inc.) were added. Sterile distilled water was added thereto so that the total volume was 10 μL, and the mixture was allowed to react at 15° C. for 3 hours for ligation. This was named Ligation Liquid P.

With the use of the Ligation Liquid P, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of chloramphenicol.

A growing strain on the culture medium was subjected to liquid culture in the usual manner. Plasmid DNA was extracted from the culture and cut with the use of restriction enzyme BamHI to confirm the inserted fragment. As a result, in addition to an about 4.1-kb DNA fragment of the plasmid pCRB1, an about 2.4-kb inserted fragment of the aroG gene derived from *Corynebacterium glutamicum* (Ligation Liquid P) was confirmed.

Figure 4:
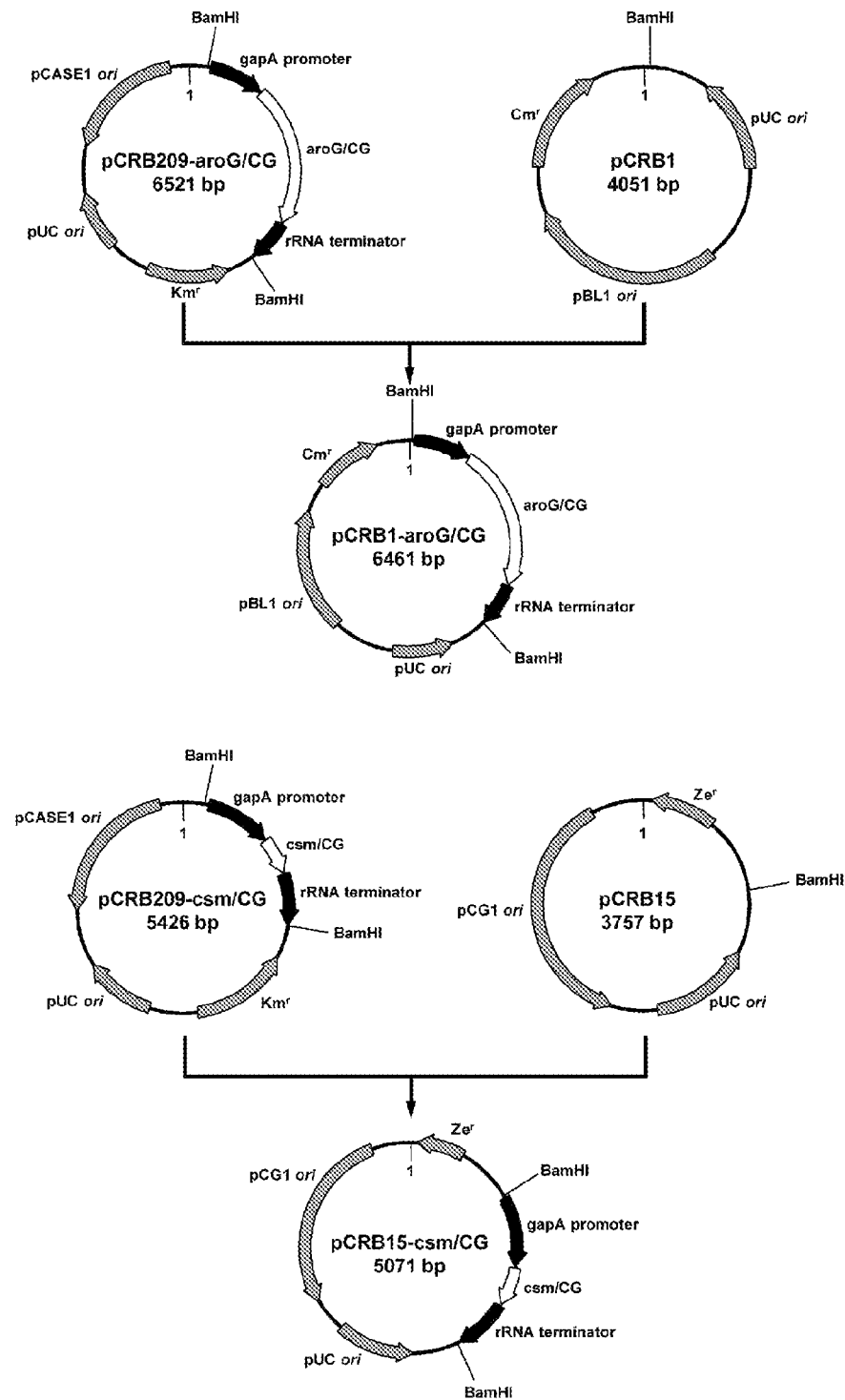
FIG. 4 shows construct of various plasmids used in Examples.

The plasmid comprising the aroG gene derived from *Corynebacterium glutamicum* was named pCRB1-aroG/CG (FIG. 4).

Cloning of Phenol-Producing Gene to pCRB15

The above plasmid pCRB209-csm/CG was cut with the use of a restriction enzyme BamHI. After agarose gel electrophoresis, an about 1.3-kb DNA fragment recovered from the agarose gel with the use of QIAquick Gel Extraction Kit (made by QIAGEN), in which fragment a gapA promoter, a csm gene derived from *Corynebacterium glutamicum*, and a terminator sequence were ligated, and an about 3.8-kb DNA fragment obtained by BamHI digestion of the plasmid pCRB15, followed by 10 min-treatment at 70° C. for deactivation of BamHI were mixed. To this, 1 µL of T4 DNA ligase 10× buffer solution and 1 unit of T4 DNA ligase (made by Takara Bio, Inc.) were added. Sterile distilled water was added thereto so that the total volume was 10 µL, and the mixture was allowed to react at 15° C. for 3 hours for ligation. This was named Ligation Liquid Q.

With the use of the Ligation Liquid Q, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 25 µg/mL of zeocin.

A growing strain on the culture medium was subjected to liquid culture in the usual manner. Plasmid DNA was extracted from the culture and cut with the use of restriction enzyme BamHI to confirm the inserted fragment. As a result, in addition to an about 3.8-kb DNA fragment of the plasmid pCRB15, an about 1.3-kb inserted fragment of the csm gene derived from *Corynebacterium glutamicum* (Ligation Liquid Q) was confirmed.

The plasmid comprising the csm gene derived from *Corynebacterium glutamicum* was named pCRB15-csm/CG (FIG. 4).

(5) Construction of Plasmids for *Corynebacterium glutamicum* Chromosomal Gene Disruption Construction of Plasmid for *Corynebacterium glutamicum* pheA Gene Disruption A DNA fragment required for constructing a plasmid for markerless disruption of the pheA gene on the chromosome of *Corynebacterium glutamicum* was amplified by the PCR method as described below.

In the PCR, the following set of primers was synthesized based on the sequence of *Corynebacterium glutamicum* R with the use of "394 DNA/RNA Synthesizer" made by Applied Biosystems, and was used.

Primers for Amplification of pheA-1 Region (a-19);
(SEQ ID NO: 54)
5'-CTCT CTGCAG TGAAGTGCGTGTAAACGCAC-3'

(b-19);
(SEQ ID NO: 55)
5'-GCTTAGCTAGTTGGTCGGTTGCAATGATTTGCACGTTGGAG-3'

Primer (a-19) has a PstI restriction enzyme site added thereto.

Primers for Amplification of pheA-2 Region (SEQ ID NO: 56)
(a-20); 5'-AACCGACCAACTAGCTAAGC-3'

(SEQ ID NO: 57)
(b-20); 5'-CTCT TCTAGA AATTACTCCTGCCATGGCA G-3'

Primer (a-20) has an XbaI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10X LA PCR ™ Buffer II (Mg²⁺ free) | 5 µL |
| 25 mM MgCl₂ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 µL of the reaction mixture was subjected to PCR.
*⁾For amplification of the pheA-1 region, a combination of primers (a-19) and (b-19), and for amplification of the pheA-2 region, a combination of primers (a-20) and (b-20) were used.

PCR Cycle:
Denaturation step: 94° C., 60 seconds
Annealing step: 52° C., 60 seconds
Extension step: 72° C.
pheA-1 region: 50 seconds
pheA-2 region: 50 seconds A cycle consisting of the above 3 steps was repeated 30 times.

Using 10 µL of the above-produced reaction mixture, 0.8% agarose gel electrophoresis was performed. An about 0.9-kb DNA fragment in the case of the *Corynebacterium glutamicum* pheA-1 region, and an about 0.8-kb DNA fragment in the case of the pheA-2 region were detected.

Subsequently, 1 µL each of the pheA-1 region fragment and the pheA-2 region fragment, which were amplified by the above PCR, were mixed and allowed to react for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10X LA PCR ™ Buffer II (Mg²⁺ free) | 5 µL |
| 25 mM MgCl₂ | 5 µL |
| dNTP Mixture (2.5 mM each) | 8 µL |
| The above 2 fragments*⁾ | 1 µL each |
| Sterile distilled water | 29.5 µL |

The above ingredients were mixed, and 50 µL of the reaction mixture was subjected to PCR.
*⁾Two kinds of fragments, namely pheA-1 region fragment and pheA-2 region fragment were used.

PCR Cycle:
Denaturation step: 95° C., 20 seconds
Annealing step: 52° C., 5 seconds
Extension step: 72° C., 50 seconds A cycle consisting of the above 3 steps was repeated 30 times.

Further, using, as the template DNA, the obtained fragment in which pheA-1 and pheA-2 were ligated, a pheA deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the pheA deletion fragment, a combination of primers (a-19) and (b-20) was used.

PCR Cycle:
 Denaturation step: 95° C., 20 seconds
 Annealing step: 52° C., 5 seconds
 Extension step: 72° C., 97 seconds
 A cycle consisting of the above 3 steps was repeated 30 times.

Using 10 μL of the above-produced reaction mixture, 0.8% agarose gel electrophoresis was performed, and an about 1.6-kb fragment of the pheA deletion fragment was detected.

10 μL of the about 1.6-kb DNA fragment of the pheA deletion fragment derived from *Corynebacterium glutamicum* R, which was amplified by the above PCR, and 2 μL of an about 4.4-kb plasmid, pCRA725 for markerless chromosomal gene transfection (J. Mol. Microbiol. Biotechnol., Vol. 8, 243-254, 2004 (JP 2006-124440 A) were cut with the use of restriction enzymes PstI and XbaI and processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 and the mixture was allowed to react at 15° C. for 3 hours for ligation. This was named Ligation Liquid R.

With the use of the Ligation Liquid R, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzymes PstI and XbaI to confirm the inserted fragment. As a result, in addition to an about 4.4-kb DNA fragment of the plasmid pCRA725, an about 1.6-kb inserted fragment of the pheA deletion gene derived from *Corynebacterium glutamicum* (Ligation Liquid R) was confirmed.

The plasmid comprising the pheA deletion gene derived from *Corynebacterium glutamicum* was named pCRA725-pheA/CG.

Construction of Plasmid for *Corynebacterium glutamicum* poxF Gene Disruption

A DNA fragment required for constructing a plasmid for markerless disruption of the poxF gene on the chromosome of *Corynebacterium glutamicum* was amplified by the PCR method as described below.

In the PCR, the following set of primers was synthesized based on the sequence of *Corynebacterium glutamicum* R with the use of "394 DNA/RNA Synthesizer" made by Applied Biosystems, and was used.

Primers for Amplification of poxF-1 Region

```
(a-21);
                                            (SEQ ID NO: 58)
   5'-CTCT TCTAGA TACGTCCTAAACACCCGAC-3'

(b-21);
                                            (SEQ ID NO: 59)
   5'-GACCAACCATTGCTGACTTGCGTATCCATAGTCAGGCTTC-3'
```

Primer (a-21) has an XbaI restriction enzyme site added thereto.

Primers for Amplification of poxF-2 Region

```
                                            (SEQ ID NO: 60)
(a-22);  5'-CAAGTCAGCAATGGTTGGTC-3'

(SEQ ID NO: 61)
(b-22);  5'-CTCT TCTAGA TGATCAGTACCAAGGGTGAG-3'
```

Primer (b-22) has an XbaI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Tag (made by Takara Bio, Inc.) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the poxF-1 region, a combination of primers (a-21) and (b-21), and for amplification of the poxF-2 region, a combination of primers (a-22) and (b-22) were used.

PCR Cycle:
 Denaturation step: 94° C., 60 seconds
 Annealing step: 52° C., 60 seconds
 Extension step: 72° C.
 poxF-1 region: 50 seconds
 poxF-2 region: 50 seconds
 A cycle consisting of the above 3 steps was repeated 30 times.

Using 10 μL of the above-produced reaction mixture, 0.8% agarose gel electrophoresis was performed. An about 0.8-kb DNA fragment in the case of the *Corynebacterium glutamicum* poxF-1 region, and an about 0.8-kb DNA fragment in the case of the poxF-2 region were detected.

Subsequently, 1 μL each of the poxF-1 region fragment and the poxF-2 region fragment, which were amplified by the above PCR, were mixed and allowed to react for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg$^{2+}$ free) | 5 μL |
| 25 mM MgCl$_2$ | 5 μL |
| dNTP Mixture (2.5 mM each) | 8 μL |
| The above 2 fragments*⁾ | 1 μL each |
| Sterile distilled water | 29.5 μL |

The above ingredients were mixed, and 50 μL of the reaction mixture was subjected to PCR.
*⁾Two kinds of fragments, namely poxF-1 region fragment and poxF-2 region fragment were used.

PCR Cycle:
Denaturation step: 95° C., 20 seconds
Annealing step: 52° C., 5 seconds
Extension step: 72° C., 50 seconds
A cycle consisting of the above 3 steps was repeated 30 times.

Further, using, as the template DNA, the obtained fragment in which poxF-1 and poxF-2 were ligated, a poxF deletion fragment was amplified by PCR.

Actual PCR was performed with the use of a thermal cycler, GeneAmp PCR System 9700 (made by Applied Biosystems) and TaKaRa LA Tag (made by Takara Bio, Inc.) as a reaction reagent under the conditions described below.

Reaction Mixture:

| | |
|---|---|
| TaKaRa LA Taq ™ (5 units/μL) | 0.5 μL |
| 10X LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the poxF deletion fragment, a combination of primers (a-21) and (b-22) was used.

PCR Cycle:
Denaturation step: 95° C., 20 seconds
Annealing step: 52° C., 5 seconds
Extension step: 72° C., 97 seconds
A cycle consisting of the above 3 steps was repeated 30 times.

Using 10 μL of the above-produced reaction mixture, 0.8% agarose gel electrophoresis was performed, and an about 1.6-kb fragment of the poxF deletion fragment was detected.

10 μL of the about 1.7-kb DNA fragment of the poxF deletion fragment derived from *Corynebacterium glutamicum* R, which was amplified by the above PCR, and 2 μL of an about 4.4-kb plasmid, pCRA725 for markerless chromosomal gene transfection (J. Mol. Microbiol. Biotechnol., Vol. 8, 243-254, 2004 (JP 2006-124440 A) were cut with the use of restriction enzyme XbaI, and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid S.

With the use of the Ligation Liquid S, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme XbaI to confirm the inserted fragment. As a result, in addition to an about 4.4-kb DNA fragment of the plasmid pCRA725, an about 1.7-kb inserted fragment of the pheA deletion gene derived from *Corynebacterium glutamicum* (Ligation Liquid S) was confirmed.

The plasmid comprising the poxF deletion gene derived from *Corynebacterium glutamicum* was named pCRA725-poxF/CG.

(6) Construction of Strain in which Genes Associated with by-Product Formation Pathway and/or Phenol Degradation are Disrupted Vector pCRA725 for markerless chromosomal gene transfection is a plasmid that cannot be replicated within *Corynebacterium glutamicum* R. With the use of the plasmid pCRA725-pheA/CG, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above medium was applied to BT agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-pheA/CG with the homologous region on the chromosome, the strain shows kanamycin resistance resulting from the expression of the kanamycin resistance gene on the pCRA725-pheA/CG and mortality in a culture medium containing sucrose resulting from the expression of the *Bacillus subtilis* sacR-sacB gene. In the case of a strain having a double crossover of the plasmid pCRA725-pheA/CG, the strain shows kanamycin sensitivity resulting from the loss of the kanamycin resistance gene on the pCRA725-pheA/CG and growing ability in a culture medium containing sucrose resulting from the loss of the sacR-sacB gene. The markerless chromosomal gene disruptant shows kanamycin sensitivity and growing ability in a culture medium containing sucrose. Therefore, a strain that showed kanamycin sensitivity and growing ability in a culture medium containing sucrose was selected.

The obtained markerless pheA gene disruptant of *Corynebacterium glutamicum* R was named *Corynebacterium glutamicum* PHE1 (Table 1).

In a similar manner, with the use of the plasmid pCRA725-poxF/CG constructed in the above (5) for markerless disruption of the *Corynebacterium glutamicum* R poxF gene, which encodes an enzyme having phenol 2-monooxygenase activity, transformation of a *Corynebacterium glutamicum* ΔpheA strain was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin. The single crossover strain obtained in the above culture medium was applied to BT agar medium containing 10% (w/v) sucrose, and selection was performed based on kanamycin sensitivity and growing ability in a culture medium containing sucrose.

The obtained markerless pheA and poxF gene disruptant was named *Corynebacterium glutamicum* PHE2 (Table 1).

TABLE 1

Corynebacterium glutamicum chromosomal gene disruptant

| Strain | Disrupted chromosomal gene | |
|---|---|---|
| PHE-1 | ΔpheA | |
| PHE-2 | ΔpheA | ΔpoxF |

(7) Construction of Transgenic Strain for tpl Enzyme Gene Having Tyrosine Phenol-Lyase Activity With the use of each of the above-described 6 kinds of plasmids pCRB209-tpl/PA, pCRB207-tpl/CB, pCRB210-tpl/DH, pCRB209-tpl/CA, pCRB209-tpl/NP, and pCRB209-tpl/TD, transformation of Corynebacterium glutamicum R was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted fragment. As a result, transfection of the above-prepared plasmids pCRB209-tpl/PA, pCRB207-tpl/CB, pCRB210-tpl/DH, pCRB209-tpl/CA, pCRB209-tpl/NP, and pCRB209-tpl/TD was confirmed.

The obtained strains were named Corynebacterium glutamicum R/pCRB209-tpl/PA, R/pCRB207-tpl/CB, R/pCRB210-tpl/DH, R/pCRB209-tpl/CA, R/pCRB209-tpl/NP, and R/pCRB209-tpl/TD.

(8) Construction of Transgenic Strain for Phenol Production Gene

With the use of the above-described plasmid pCRB209-tpl/PA, transformation of Corynebacterium glutamicum R was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, transfection of the above-constructed plasmid pCRB209-tpl/PA was confirmed.

The obtained strain was named Corynebacterium glutamicum PHE3.

Also, with the use of the above-described plasmids pCRB209-tpl/PA and pCRB1-aroG/CG, transformation of Corynebacterium glutamicum R was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin and 5 μg/mL of chloramphenicol. These two kinds of plasmids can coexist in Corynebacterium glutamicum.

A growing strain on the culture medium was subjected to liquid culture in the usual manner. Plasmid DNA was extracted from the culture and cut with the use of restriction enzymes to confirm the inserted fragment. As a result, transfection of the above-constructed plasmids pCRB209-tpl/PA and pCRB1-aroG/CG was confirmed.

The obtained strain was named Corynebacterium glutamicum PHE4.

With the use of the plasmids pCRB209-tpl/PA, pCRB1-aroG/CG, and pCRB15-csm/CG, transformation of Corynebacterium glutamicum R was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin, 5 μg/mL of chloramphenicol, and 25 μg/mL of zeocin. These three kinds of plasmids can coexist in Corynebacterium glutamicum.

A growing strain on the culture medium was subjected to liquid culture in the usual manner. Plasmid DNA was extracted from the culture and cut with the use of restriction enzymes to confirm the inserted fragment. As a result, transfection of the above-constructed plasmids pCRB209-tpl/PA, pCRB1-aroG/CG, and pCRB15-csm/CG was confirmed. The obtained strain was named Corynebacterium glutamicum PHE5. The outline of gene recombination in the above-obtained strains is shown in Table 2.

TABLE 2

Transgenic strains for phenol production gene

| Strain | Host strain | Transfected gene name/origin | | |
|---|---|---|---|---|
| PHE-3 | Corynebacterium | tpl/PA | | |
| PHE-4 | glutamicum R | tpl/PA | aroG/CG | |
| PHE-5 | (wild strain) | tpl/PA | aroG/CG | csm/CG |

*) Abbreviations in Table 2 stand for the following.

<Abbreviation for gene origin>

PA: Pantoea agglomerans

CG: Corynebacterium glutamicum R (9) Transfection of Phenol-Producing Gene into Strain in which by-Product Formation Pathway and Phenol-Degrading Genes are Disrupted Further, with the use of the plasmids pCRB209-tpl/PA, pCRB1-aroG/CG, and pCRB15-csm/CG, transformation of Corynebacterium glutamicum PHE1 (ΔpheA) and PHE2 (ΔpheAΔpoxF) strains were performed by electroporation (Agric. Biol. Chem., Vol. 54, 443-447 (1990) and Res. Microbiol., Vol. 144, 181-185 (1993)), and the strains were applied to A agar medium containing 50 μg/mL of kanamycin, 5 μg/mL of chloramphenicol, and 25 μg/mL of zeocin. These three kinds of plasmids can coexist in Corynebacterium glutamicum.

A growing strain on the culture medium was subjected to liquid culture in the usual manner. Plasmid DNA was extracted from the culture and cut with the use of restriction enzymes to confirm the inserted fragment. As a result, transfection of the above-constructed plasmids pCRB209-tpl/PA, pCRB1-aroG/CG, and pCRB15-csm/CG was confirmed. The obtained transformant of the PHE1 (ΔpheA) strain was named Corynebacterium glutamicum PHE6, and the obtained transformant of the PHE2 (ΔpheAΔldhA) strain was named Corynebacterium glutamicum PHE7. The outline of gene recombination in the above-obtained strains is shown in Table 6. Corynebacterium glutamicum PHE7 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-976 on Aug. 12, 2011 (the original deposit was made under Accession Number NITE P-976 on Aug. 31, 2010).

TABLE 3

Transfection of phenol-producing genes into gene disrupted strains

| Strain | C. glutamicum disrupted chromosomal gene | Transfected gene name/origin |
|---|---|---|
| PHE-6 | ΔpheA | tpl/PA, aroG/CG, csm/CG |
| PHE-7 | ΔpheA ΔpoxF | |

*) Abbreviations in Table 3 stand for the following.
<Abbreviation for gene origin>
PA: *Pantoea agglomerans*
CG: *Corynebacterium glutamicum* R

Example 3

Tyrosine Phenol-Lyase Activity Determination in Transgenic Strains for tpl Gene
(1) Tyrosine Phenol-Lyase Activity Determination

*Corynebacterium glutamicum* R/pCRB209-tpl/PA, R/pCRB207-tpl/CB, R/pCRB210-tpl/DH, R/pCRB209-tpl/CA, R/pCRB209-tpl/NP, and R/pCRB209-tpl/TD, which were each constructed in Example 2 (7) by transfection of a tyrosine phenol-lyase gene were applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06 w/v % $Fe_2SO_4.7H_2O$+0.042 w/v % $MnSO_4.2H_2O$, 1 mL of 0.02 w/v % biotin solution, 2 mL of 0.01 w/v % thiamin solution, 2 g of yeast extract, 7 g of vitamin assay casamino acid, 40 g of glucose, and 15 g of agar suspended in 1 L of distilled water) containing 50 μg/mL of kanamycin, and left stand in the dark at 28° C. for 20 hours.

An inoculation loop of each *Corynebacterium glutamicum* transgenic strain for a tyrosine phenol-lyase gene grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06 w/v % $Fe_2SO_4.7H_2O$+0.042 w/v % $MnSO_4.2H_2O$, 1 mL of 0.02 w/v % biotin solution, 2 mL of 0.01 w/v % thiamin solution, 2 g of yeast extract, 7 g of vitamin assay casamino acid, and 40 g of glucose suspended in 1 L of distilled water) containing 50 μg/mL of kanamycin, and aerobically cultured with shaking at 33° C. for 16 hours.

The transgenic strain for a tyrosine phenol-lyase gene grown in the above conditions was inoculated into 100 mL of A liquid medium containing 50 μg/mL of kanamycin, and aerobically cultured with shaking at 33° C. for 16 hours. *Corynebacterium glutamicum* R was cultured in the same conditions except that the A medium did not contain kanamycin.

Each kind of the bacterial cells cultured and proliferated as above was collected by centrifugation (8,000×g at 4° C. for 10 minutes). After crushing bacterial cells with the use of glass beads, centrifugation (15,000 rpm, 20 minutes) was performed. With the use of the obtained crushed cell supernatant as a crude enzyme liquid, Tpl activity was determined by the following method.

50 mM potassium phosphate buffer at pH 8.0, 2.5 mM L-Tyr, 0.1 mM pyridoxal phosphate, 20% glycerol, and the crude enzyme liquid were mixed and allowed to react at 30° C. for 30 minutes. The reaction was stopped by the addition of 0.6 N hydrochloric acid (final concentration). After filter filtration, the produced phenol was analyzed and quantified by HPLC (Cosmosil C18 AR11, mobile phase: 20% MeOH and 0.07% perchloric acid). The enzyme specific activity determined based on the amount of phenol produced by the enzyme reaction is shown in Table 4.

As a result, the *Corynebacterium glutamicum* expressing the tpl gene derived from *Pantoea agglomerans*, the tpl gene derived from *Citrobacter braakii*, or the tpl gene derived from *Desulfitobacterium hafniense* showed particularly high activity, and also the *Corynebacterium glutamicum* expressing the tpl gene derived from *Chloroflexus aurantiacus*, the tpl gene derived from *Nostoc punctiforme*, or the tpl gene derived from *Treponema denticola* showed a certain activity.

TABLE 4

Activity determination in *Corynebacterium glutamicum* transgenic strains for tpl gene

| Strain | Transferred gene | Specific activity (U/mg-protein) |
|---|---|---|
| R/pCRB209-tpl/PA | tpl(*Pantoea agglomerans*) | 0.027 |
| R/pCRB207-tpl/CB | tpl(*Citrobacter braakii*) | 0.052 |
| R/pCRB210-tpl/DH | tpl(*Desulfitobacterium hafniense*) | 0.029 |
| R/pCRB209-tpl/CA | tpl(*Chloroflexus aurantiacus*) | 0.001 |
| R/pCRB209-tpl/NP | tpl(*Nostoc punctiforme*) | 0.001 |
| R/pCRB209-tpl/TD | tpl(*Treponema denticola*) | 0.002 |
| *Corynebacterium glutamicum* R | | 0 |

Example 4

Experiment of Phenol Production Using *Corynebacterium glutamicum* Transgenic Strains for Phenol-Producing Gene In order to examine the effects of the *Pantoea agglomerans* tpl gene, which encodes an enzyme having tyrosine phenol-lyase activity, the *Corynebacterium glutamicum* aroG gene, which encodes DAHP synthetase, and the *Corynebacterium glutamicum* csm gene, which encodes chorismate mutase, these genes were transferred into *Corynebacterium glutamicum* R in a one-by-one stacking manner for comparison of phenol production.

The PHE3 strain (transgenic for tpl gene), PHE4 strain (transgenic for tpl gene and aroG gene), and PHE5 strain (transgenic for tpl gene, aroG gene, and csm gene), all of which were constructed in Example 2 (see Table 2), were applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06 w/v % $Fe_2SO_4.7H_2O$+0.042 w/v % $MnSO_4.2H_2O$, 1 mL of 0.02 w/v % biotin solution, 2 mL of 0.01 w/v % thiamin solution, 2 g of yeast extract, 7 g of vitamin assay casamino acid, 40 g of glucose, and 15 g of agar suspended in 1 L of distilled water) containing 50 μg/mL of kanamycin in the case of PHE3, 50 μg/mL of kanamycin and 5 μg/mL of chloramphenicol in the case of PHE4, or 50 μg/mL of kanamycin, 5 μg/mL of chloramphenicol, and 25 μg/mL of zeocin in the case of PHE5, and left stand in the dark at 28° C. for 20 hours.

An inoculation loop of each *Corynebacterium glutamicum* transgenic strain for a single gene grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06 w/v % $Fe_2SO_4.7H_2O$+0.042 w/v % $MnSO_4.2H_2O$, 1 mL of 0.02 w/v % biotin solution, 2 mL of 0.01 w/v % thiamin solution, 2 g of yeast extract, 7 g of vitamin assay casamino acid, and 40 g of glucose suspended in 1 L of distilled water) containing the corresponding antibiotic(s), and aerobically cultured with shaking at 28° C. for 15 hours.

The transgenic strain for a phenol-producing gene grown in the above conditions was inoculated into 100 mL of A liquid medium containing the corresponding antibiotic(s), and aerobically cultured with shaking at 33° C. for 24 hours. For quantitative determination of phenol, the reaction mixture sampled was centrifuged (15,000×g at 4° C. for 10 minutes), and the obtained supernatant was analyzed by liquid chromatography.

The results are shown in Table 5. *Corynebacterium glutamicum* PHE3 produced 0.1 mM of phenol, *Corynebacterium glutamicum* PHE4 produced 0.4 mM of phenol, and *Corynebacterium glutamicum* PHE5 produced 0.9 mM of phenol in the respective culture media in 24 hours. That is, phenol production from glucose was enabled by the transfer of the tpl gene, and the increase in the amount of produced phenol was achieved by the altered metabolism resulting from the transfer of the aroG gene and the csm gene.

TABLE 5

Experiment of phenol production using transgenic strains for phenol production gene

| Strain | Host strain | Transfected gene name/origin | | | Amount of produced phenol (mM) |
|---|---|---|---|---|---|
| PHE-3 | *Corynebacterium* | tpl/PA | | | 0.1 |
| PHE-4 | *glutamicum* R | tpl/PA | aroG/CG | | 0.4 |
| PHE-5 | (wild strain) | tpl/PA | aroG/CG | csm/CG | 0.9 |

*) Abbreviations in Table 5 stand for the following.
<Abbreviation for gene origin>
PA: *Pantoea agglomerans*
CG: *Corynebacterium glutamicum* R Example 5

Experiment of Phenol Production Using Transgenic Strains for Phenol-Producing Gene in which by-Product Formation Pathway and Phenol-Degrading Genes are Disrupted The markerless *Corynebacterium glutamicum* chromosome gene disruptants, PHE6 (ΔpheA) and PHE7 (ΔpheAΔpoxF), constructed in Example 2 by transferring the phenol-producing gene expression plasmids pCRB209-tpl/PA, pCRB1-aroG/CG, and pCRB15-csm/CG, were applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar suspended in 1 L of distilled water) containing 50 μg/mL of kanamycin, 5 μg/mL of chloramphenicol, and 25 μg/mL of zeocin, and left stand in the dark at 28° C. for 20 hours (Table 6).

An inoculation loop of each transgenic strain for a phenol-producing gene grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose suspended in 1 L of distilled water) containing 50 μg/mL of kanamycin, 5 μg/mL of chloramphenicol, and 25 μg/mL of zeocin, and aerobically cultured with shaking at 33° C. for 16 hours.

The transgenic strain for a phenol-producing gene grown in the above conditions was inoculated into 100 mL of A liquid medium containing 50 μg/mL of kanamycin, 5 μg/mL of chloramphenicol, and 25 μg/mL of zeocin, and aerobically cultured with shaking at 33° C. for 24 hours.

For quantitative determination of phenol, the reaction mixture sampled was centrifuged (15,000×g at 4° C. for 10 minutes), and the obtained supernatant was analyzed by liquid chromatography.

As a result, while PHE5 using a *Corynebacterium glutamicum* wild strain as a host produced 0.9 mM of phenol in 24 hours, PHE6 using a *Corynebacterium glutamicum* pheA gene disruptant as a host produced 5.8 mM of phenol, and PHE7 using a *Corynebacterium glutamicum* pheA and poxF gene disruptant as a host produced 6.9 mM of phenol.

That is, metabolically engineered alteration by pheA gene disruption, which blocks the pathway for producing phenylalanine as a by-product, and by poxF gene disruption, which blocks the degradation pathway for phenol, sequentially improved the phenol productivity.

TABLE 6

Experiment of phenol production using transgenic strains for phenol-producing gene in which by-product formation pathway and phenol-degrading genes are disrupted

| Strain | Transfected gene | Disrupted host chromosomal gene | | Amount of produced phenol (mM) |
|---|---|---|---|---|
| PHE5 | tpl/PA aroG/CG | *Corynebacterium glutamicum* (wild strain) | | 0.9 |
| PHE6 | csm/CG | ΔpheA | | 5.8 |
| PHE7 | | ΔpheA | ΔpoxF | 6.9 |

*) Abbreviations in the table stand for the following.
<Abbreviation for gene origin>
PA: *Pantoea agglomerans*
CG: *Corynebacterium glutamicum*

Example 6

Experiment of Phenol Production Using *Corynebacterium glutamicum* PHE7 Under Reducing Conditions The *Corynebacterium glutamicum* phenol-producing strain PHE7 created in Example 2 was applied to A agar medium containing 50 μg/mL of kanamycin, 5 μg/mL of chloramphenicol, and 25 μg/mL of zeocin, and left stand in the dark at 28° C. for 20 hours.

An inoculation loop of the *Corynebacterium glutamicum* phenol-producing strain PHE7 grown on a plate as above was inoculated into a test tube containing 10 mL of A liquid medium containing 50 μg/mL of kanamycin, 5 μg/mL of chloramphenicol, and 25 μg/mL of zeocin, and aerobically cultured with shaking at 28° C. for 15 hours.

The *Corynebacterium glutamicum* phenol-producing strain PHE7 grown in the above conditions was inoculated into a 2 L-conical flask containing 500 mL of A liquid medium containing 50 μg/mL of kanamycin, 5 μg/mL of chloramphenicol, and 25 μg/mL of zeocin, and aerobically cultured with shaking at 28° C. for 15 hours.

Each kind of the bacterial cells cultured and proliferated as above was collected by centrifugation (5,000×g at 4° C. for 15 minutes). The obtained bacterial cells were suspended in BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was $OD_{610}$=35. To 100-mL medium bottles containing 60 mL of the cell suspension, glucose was added so as to be 8% in concentration, and the reaction was allowed to proceed under reducing conditions (the ORP of the reaction mixture: −450 mV) in a water bath kept at 33° C. with stirring. During the reaction, 2.5 N aqueous ammonia was added with the use of a pH controller (Type: DT-1023 made by Able) to avoid the pH of the reaction mixture falling below 7.0.

A sample of the reaction mixture was centrifuged (15,000×g at 4° C. for 10 minutes), and the obtained supernatant was used for quantitative determination of phenol.

As a result, in the reaction under reducing conditions, the *Corynebacterium glutamicum* phenol-producing strain PHE7 exhibited higher productivity than in the aerobic culture and had produced 11.3 mM of phenol 24 hours after the start of the reaction.

Industrial Applicability

According to the process of the present invention, phenol can be produced with a practical efficiency using microorganisms.

The invention claimed is:

1. A phenol-producing transformant constructed by transferring a gene which encodes an enzyme having tyrosine phenol-lyase activity into a *Corynebacterium* as a host,
   wherein the gene which encodes an enzyme having tyrosine phenol-lyase activity is a DNA consisting of the nucleotide sequence of SEQ ID NO: 36, SEQ ID NO: 39, SEQ ID NO: 42, SEQ ID NO: 45, SEQ ID NO: 48 or SEQ ID NO: 51;
   a gene which encodes an enzyme having DAHP (3-deoxy-D-arabino-heptulosonate 7-phosphate) synthase activity aroG of the *Cornybacterium* and a gene which encodes an enzyme having chorismate mutase activity of the *Cornyebacterium* as the host are highly expressed, and
   a gene which encodes an enzyme having prephenate dehydratase activity on the chromosome of the *Cornyebacterium* as the host is disrupted or deleted.

2. The transformant of claim 1, wherein a gene which encodes an enzyme having phenol 2-monooxygenase activity on the chromosome of the *Cornyebacterium* as the host has a disruption or deletion.

3. The transformant of claim 1, wherein the *Cornyebacterium* as the host is *Corynebacterium glutamicum*,
   the gene which encodes the enzyme having DAHP (3-deoxy-D-arabino-heptulosonate 7-phosphate) synthase activity aroG of the *Corynebacterium glutamicum* and the gene which encodes the enzyme having chorismate mutase activity of *Corynebacterium glutamicum* R (FERM BP-18976), ATCC13032, or ATCC13869 as the host are highly expressed, and
   the gene which encodes the enzyme having prephenate dehydratase activity on the chromosome of *Corynebacterium glutamicum* R (FERM BP-18976), ATCC13032, or ATCC13869 as the host *Corynebacterium glutamicum* is disrupted or deleted.

4. A *Corynebacterium glutamicum* transformant PHE7 (Accession Number: NITE BP-976).

5. A process for producing phenol, which comprises a step of reacting the transformant of claim 1 in a reaction mixture containing a saccharide under reducing conditions, and a step of collecting phenol from the reaction mixture.

6. The process of claim 5, wherein the transformant does not substantially proliferate in the reaction step.

7. The process of claim 5, wherein the oxidation-reduction potential of the reaction mixture under reducing conditions is −200 mV to −500 mV.

8. The process of claim 5, wherein the saccharide is selected from a group consisting of glucose, fructose, mannose, xylose, arabinose, galactose, sucrose, maltose, lactose, cellobiose, trehalose, and mannitol.

* * * * *